(12) United States Patent
Dugar

(10) Patent No.: US 7,393,851 B2
(45) Date of Patent: Jul. 1, 2008

(54) AZAINDOLE DERIVATIVES AS INHIBITORS OF P38 KINASE

(75) Inventor: Sundeep Dugar, San Jose, CA (US)

(73) Assignee: Scios, Inc., Mountain View, CA (US)

( * ) Notice: Subject to any disclaimer, the term of this patent is extended or adjusted under 35 U.S.C. 154(b) by 411 days.

(21) Appl. No.: 10/683,656

(22) Filed: Oct. 9, 2003

(65) Prior Publication Data
US 2004/0176598 A1    Sep. 9, 2004

Related U.S. Application Data

(60) Provisional application No. 60/417,599, filed on Oct. 9, 2002.

(51) Int. Cl.
*A61K 31/495* (2006.01)
*C07D 471/02* (2006.01)
(52) U.S. Cl. ........................ 514/255; 544/362
(58) Field of Classification Search ............ 514/255; 544/362
See application file for complete search history.

(56) References Cited

U.S. PATENT DOCUMENTS

| | | | | |
|---|---|---|---|---|
| 6,476,045 | B1 | 11/2002 | Dinnell et al. | 514/300 |
| 6,649,636 | B1 * | 11/2003 | Ando et al. | 514/341 |
| 6,897,207 | B2 * | 5/2005 | Cox et al. | 514/183 |
| 2002/0183319 | A1 | 12/2002 | Liang et al. | 514/234.5 |
| 2005/0209269 | A1 * | 9/2005 | Salom et al. | 514/300 |
| 2005/0256151 | A1 * | 11/2005 | Salom et al. | 514/300 |
| 2006/0046977 | A1 * | 3/2006 | Nunes et al. | 514/63 |

FOREIGN PATENT DOCUMENTS

| | | |
|---|---|---|
| WO | WO 96/40143 | 12/1996 |
| WO | WO 97/26252 | 7/1997 |
| WO | WO 98/06715 | 2/1998 |
| WO | WO 98/07425 | 2/1998 |
| WO | WO 99/61426 | 12/1999 |
| WO | WO 00/12074 | 3/2000 |
| WO | WO 00/59904 | 10/2000 |
| WO | WO 00/71535 | 11/2000 |
| WO | WO 2004/032874 A2 | 4/2004 |

OTHER PUBLICATIONS

Janssens et al. "Bicyclic heterocycliyl . . ." Ca 104:68856 (1986).*
Houpis et al. "Synthesis of functionalized . . ." CA 122:105718 (1995).*
Furuya et al. "Preparation of thieno . . ." Ca 124:202226 (1995).*
Buzzetti et al. "Preparation and formulation . . ." CA 124:260834 (1996).*
Kim et al. "Piperazinecarboxamide . . ." CA 125:58548 (1996).*
Suzuki et al. "preparation of condensed . . ." Ca 127:135807 (1997).*
Ewing et al. "Substituted piperazinone . . ." CA 131:130007 (1999).*
Salom et al. "Preparation of pyrrolo[2,3-b]pyridine . . ." CA 143:133351 (2005).*
Salom et al. "Preparation of . . ." CA 143:347150 (2005).*
Ledeboer et al. "Pyrrolopyridines . . ." CA 146:27814 (2006).*
Saavedra et al. "preparation of thienopyridine . . ." CAS AN 2007:17769 (2007).*
Bundgaard "design of prodrugs" p. 1, 27-28 (1986).*
King "Bioisosters . . ." Med. chem. principle and Practice p. 206-208 (1994).*
Patani et al. "Bioisosterism . . ." Chem Rev. v90 p. 3147, 3168 (1990).*
International Search Report mailed on Apr. 13, 2004 for PCT patent application No. PCT/US03/32171 filed on Oct. 9, 2003, 4 pages.
U.S. Appl. No. 60/395,693, filed Jul. 11, 2002.
Colvin et al., Tetrahedron Lett. (1982) 23(37):3835-3836.
Jiang et al., J. Biol. Chem. (1996) 271:17920-17926.
Kumar et al., Biochem. Biophys. Res. Comm. (1997) 235:533-538.
Li et al., Biochem. Biophys. Res. Comm. (1996) 228:334-340.
Rewcastle et al., J. Med. Chem. (1996) 39:1823-1835.
Stein et al., J. Biol. Chem. (1997) 272:19509-19517.
Wang et al., J. Biol. Chem. (1997) 272:23668-23674.
Ngo et al., In the Protein Folding Problem and Tertiary Structure Prediction, 1994, Merz et al., (ed.), Birkhauser, Boston, MA, pp. 433 and 492-495, Ref-U, Form-892.
Mavunkel et al., Bioorganic and Medicinal Chemistry Letters, 2003, vol. 13, pp. 3087-3090.
International Search Report Mailed on Aug. 18, 2005 for PCT/US2005/12969 filed on Apr. 15, 2005.

* cited by examiner

*Primary Examiner*—Celia Chang
(74) *Attorney, Agent, or Firm*—Morrison & Foerster LLP

(57) ABSTRACT

The invention is directed to methods to inhibit p38 kinase, preferably p38-α using compounds which are azaindoles wherein the azaindoles are coupled through a piperidine or piperazine type linker to another cyclic moiety.

16 Claims, No Drawings

… (1)

AZAINDOLE DERIVATIVES AS INHIBITORS OF P38 KINASE

RELATED APPLICATIONS

This application claims priority to U.S. Provisional Patent Application No. 60/417,599, filed Oct. 9, 2002, which is hereby incorporated by reference in its entirety.

FIELD OF THE INVENTION

The invention relates to compounds useful in treating various disorders associated with enhanced activity of kinase p38. More specifically, it concerns compounds that are related to azaindole coupled through piperazine or piperidine moieties to an aryl group as useful in these methods.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, chronic obstructive pulmonary disease, cystic fibrosis, silicosis, pulmonary sarcosis, bone fracture healing, bone resorption diseases such as osteoporosis, soft tissue damage, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

Certain aroyl/phenyl-substituted piperazines and piperidines which inhibit p38-α kinase are described in PCT publication WO00/2074 published 9 Mar. 2000. In addition, indolyl substituted piperidines and piperazines which inhibit this enzyme are described in PCT publication No. WO99/61426 published 2 Dec. 1999. Carbolene derivatives of piperidine and piperazine as p38-α inhibitors are described in PCT publication WO 00/59904 published 12 Oct. 2000. Additional substitutions on similar compounds are described in PCT publication WO00/71535 published 30 Nov. 2000. The disclosure of these documents is incorporated herein by reference.

DISCLOSURE OF THE INVENTION

The invention is directed to methods and compounds useful in treating conditions that are characterized by enhanced p38 activity. These conditions include inflammation, proliferative diseases, and certain cardiovascular disorders as well as Alzheimer's disease as further described below.

Compounds of the invention have been found to inhibit p38 kinase, the α-isoform in particular, and are thus useful in treating diseases mediated by these activities. The compounds of the invention are of the formula

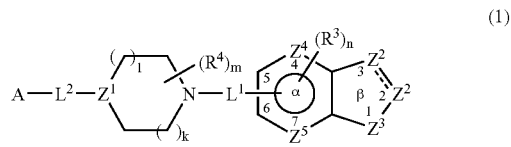

and the pharmaceutically acceptable salts thereof, or a pharmaceutical composition thereof, wherein
⤳ represents a single or double bond;
each $Z^2$ is independently $CR^1$, $C(R^1)_2$, or N wherein each $R^1$ is independently hydrogen or noninterfering substituent;
$Z^3$ is $NR^7$, O, or S;
$R^7$ is hydrogen or a non-interfering substituent;
each of $Z^4$ and $Z^5$ is independently N or $CR^1$ wherein $R^1$ is as defined above and wherein at least one of $Z^4$ and $Z^5$ is N;
each $R^3$ is independently a noninterfering substituent;
n is 0-3;
each of $L^1$ and $L^2$ is a linker;
each $R^4$ is independently a noninterfering substituent;
m is 0-4;
$Z^1$ is $CR^5$ or N wherein $R^5$ is hydrogen or a noninterfering substituent;
each of l and k is an integer from 0-2 wherein the sum of l and k is 0-3;
A is a cyclic group substituted with 0-5 noninterfering substituents, wherein two said noninterfering substituents can form a fused ring; and
the distance between the atom of A linked to $L^2$ and the center of the α ring is preferably 4.5-24 Å.

MODES OF CARRYING OUT THE INVENTION

The compounds of formula (1) are useful in treating conditions which are characterized by overactivity of p38 kinase, in particular the α-isoform. Conditions "characterized by enhanced p38 activity" include those where this enzyme is present in increased amount or wherein the enzyme has been modified to increase its inherent activity, or both. Thus, "enhanced activity" refers to any condition wherein the effectiveness of these proteins is undesirably high, regardless of the cause.

The compounds of the invention are useful in conditions where p38 kinase shows enhanced activity. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states and traumatic or surgical wounds. These conditions, of course, would be benefited by compounds which inhibit p38. Methods of treatment with the compounds of the invention are further discussed below.

The Invention Compounds

The compounds useful in the invention are derivatives of azaindole.

In the description above, certain positions of the molecule are described as permitting "noninterfering substituents." This terminology is used because the substituents in these positions generally speaking are not relevant to the essential activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound of formula (1) to inhibit p38 activity qualitatively intact. Thus, the substituent may alter the degree of inhibition of p38. However, as long as the compound of formula (1) retains the ability to inhibit p38 activity, the substituent will be classified as "noninterfering." A number of assays for determining the ability of any compound to inhibit p38 activity are available in the art. A whole blood assay for this evaluation is illustrated below: the gene for p38 has been cloned and the protein can be prepared recombinantly and its activity assessed, including an assessment of the ability of an arbitrarily chosen compound to interfere with this activity. The essential features of the molecule are tightly defined. The positions which are occupied by "noninterfering substituents" can be substituted by conventional organic moieties as is understood in the art. It is irrelevant to the present invention to test the outer limits of such substitutions. The essential features of the compounds are those set forth with particularity herein.

In addition, $L^1$ and $L^2$ are described herein as linkers that impart a distance between portions of the molecule. Typical linkers include substituted or unsubstituted alkylene, i.e., $(CH_2)_n$, wherein the use of "n" is a generic designation for a number in general as in the "nth degree" or "where $CH_2$ occurs n times", alkenylene, i.e., an alkylene moiety which contains a double bond, including a double bond at one terminus, and alkynylene, i.e., an alkylene moiety which contains a triple bond. Other suitable linkers include, for example, substituted alkenylene or alkenylenes, and carbonyl or sulfonyl moieties and the like.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

As used herein, "inorganic residue" refers to a residue that does not contain carbon. Examples include, but are not limited to, halo, hydroxy, $NO_2$ or $NH_2$.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1-2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety.

When the compounds of formula (1) contain one or more chiral centers, the invention includes optically pure forms as well as mixtures of stereoisomers or enantiomers.

With respect to the portion of the compound between the atom of Ar bound to $L^2$ and ring α, $L^1$ and $L^2$ are linkers which space the substituent Ar from ring α at a distance in a range preferably from 4.5 to 24 Å, preferably less than 24 Å, more preferably less than 20 Å, and still more preferably less than 15 Å. The distance is measured from the center of the α ring to the atom of Ar to which the linker $L^2$ is attached. Typical, but nonlimiting, embodiments of $L^1$ and $L^2$ are CO and isosteres thereof which can be subsequently converted to an oxime, an oximeether, an oximeester, or a ketal, or optionally substituted isosteres, or longer chain forms. $L^2$, in particular, may be alkylene or alkenylene optionally substituted with noninterfering substituents or $L^1$ or $L^2$ may be or may include a heteroatom such as N, S or O. Such substituents include, but are limited to, a moiety selected from the group consisting of alkyl, alkenyl, alkynyl, aryl, arylalkyl, acyl, aroyl, heteroaryl, heteroalkyl, heteroalkenyl, heteroalkynyl, heteroarylalkyl, NH-aroyl, arylacyl, heteroarylacyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, wherein two substituents can be joined to form a carbonyl moiety or an oxime, oximeether, oximeester or ketal of said carbonyl moiety.

Isosteres of CO and $CH_2$, include SO, $SO_2$, or CHOH. CO and $CH_2$ are preferred.

A is a cyclic moiety, including aryl, heteroaryl, cycloaliphatic and cycloheteroaliphatic that can be optionally substituted. A may be, for instance, cyclohexyl, piperazinyl, benzimidazolyl, morpholinyl, pyridyl, pyrimidyl, phenyl, naphthyl and the like. A is preferably substituted or unsubstituted aryl or heteroaryl, and more preferably optionally substituted phenyl.

Each substituent on A is independently a hydrocarbyl residue (1-20C) containing 0-5 heteroatoms selected from O, S and N, or is an inorganic residue. Preferred substituents include those selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, arylacyl, heteroarylacyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3-8 members. More preferred substituents include halo, alkyl (1-4C) and more preferably, fluoro, chloro and methyl. These substituents may occupy all available positions of the ring of A, preferably disubstituted, more preferably mono-substituted. These substituents may be optionally substituted with substituents similar to those listed. Of course some substituents, such as halo, are not further substituted, as known to one skilled in the art.

Two substituents on A can be joined to form a fused, optionally substituted aromatic or nonaromatic, saturated or unsaturated ring which contains 3-8 members.

Between $L^1$ and $L^2$ is a piperidine or piperazine type moiety of the following formula:

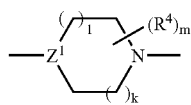

$Z^1$ is N or $CR^5$ wherein $R^5$ is H or a noninterfering substituent. Each of l and k is an integer from 0-2 wherein the sum of l and k is 0-3. The noninterfering substituents $R^5$ include, without limitation, halo, alkyl, alkoxy, aryl, arylalkyl, aryloxy, heteroaryl, acyl, carboxy, or hydroxy. Preferably, $R^5$ is H, alkyl, OR, $NR_2$, SR or halo, where R is H or alkyl. Additionally, $R^5$ can be joined with an $R^4$ substituent to form an optionally substituted non-aromatic saturated or unsaturated hydrocarbyl ring which contains 3-8 members and 0-3 heteroatoms such as O, N and/or S. Preferred embodiments include compounds wherein $Z^1$ is CH or N, and those wherein both l and k are 1.

$R^4$ represents a noninterfering substituent such as a hydrocarbyl residue (1-20C) containing 0-5 heteroatoms selected from O, S and N. Preferably $R^4$ is alkyl, alkoxy, aryl, arylalkyl, aryloxy, heteroalkyl, heteroaryl, heteroarylalkyl, RCO, acyl, halo, CN, OR, NRCOR, NR, wherein R is H, alkyl (preferably 1-4C), aryl, or hetero forms thereof. Each appropriate substituent is itself unsubstituted or substituted with 1-3 substituents. The substituents are preferably independently selected from a group that includes alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and wherein two of $R^4$ on adjacent positions can be joined to form a fused, optionally substituted aromatic or nonaromatic, saturated or unsaturated ring which contains 3-8 members, or $R^4$ is =O or an oxime, oximeether, oximeester or ketal thereof. $R^4$ may occur m times on the ring; m is an integer of 0-4. Preferred embodiments of $R^4$ comprise alkyl (1-4C), straight chain or branched, especially two alkyl substituents which may be further substituted. Most preferably $R^4$ comprises two methyl groups at positions 2 and 5 or 3 and 6 of a piperidinyl or piperazinyl ring. The substituted forms may be chiral and an isolated enantiomer may be preferred.

$R^3$ also represents a noninterfering substituent. Such substituents include hydrocarbyl residues (1-6C) containing 0-2 heteroatoms selected from O, S and/or N and inorganic residues. n is an integer of 0-3, preferably 0 or 1. Preferably, the substituents represented by $R^3$ are independently halo, alkyl, heteroalkyl, OCOR, OR, NRCOR, SR, or $NR_2$, wherein R is H, alkyl, aryl, or heteroforms thereof. More preferably $R^3$ substituents are selected from alkyl, alkoxy or halo, and most preferably methoxy, methyl, and chloro. Most preferably, n is 0 and the α ring is unsubstituted, except for $L^1$ or n is 1 and $R^3$ is halo or alkoxy, preferably methoxy.

Preferred embodiments of $R^7$ include H, optionally substituted alkyl, alkenyl, alkynyl, aryl, arylalkyl, acyl, arylacyl, aroyl, heteroaryl, heteroalkyl, heteroalkenyl, heteroalkynyl, heteroarylalkyl, heteroarylacyl, or is SOR, $SO_2R$, RCO, COOR, alkyl-COR, $SO_3R$, $CONR_2$, $SO_2NR_2$, CN, $CF_3$, $NR_2$, OR, alkyl-SR, alkyl-SOR, alkyl-$SO_2R$, alkyl-OCOR, alkyl-COOR, alkyl-CN, alkyl-$CONR_2$, or $R_3Si$, wherein each R is independently H, alkyl, alkenyl or aryl or heteroforms thereof. More preferably, $R^7$ is hydrogen or is alkyl (1-4C), preferably methyl or is acyl (1-4C), or is COOR wherein R is H, alkyl, alkenyl of aryl or hetero forms thereof. $R^7$ is also preferably a substituted alkyl wherein the preferred substituents are form ether linkages or contain sulfinic or sulfonic acid moieties. Other preferred substituents include sulfhydryl substituted alkyl substituents. Still other preferred substituents include $CONR_2$ wherein R is defined as above.

It is preferred that the indicated dotted line represents a double bond; however, compounds which contain a saturated β ring are also included within the scope of the invention.

Preferred embodiments of $R^1$ include hydrogen, alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^1$ can be joined to form a fused, optionally substituted aromatic or nonaromatic, saturated or unsaturated ring which contains 3-8 members. Most preferably, $R^1$ is H, alkyl, such as methyl, most preferably, the ring labeled a contains a double bond and $CR^1$ is CH or C-alkyl. Other preferable forms of $R^1$ include H, alkyl, acyl, aryl, arylalkyl, heteroalkyl, heteroaryl, halo, OR, $NR_2$, SR, NRCOR, alkyl-OOR, RCO, COOR, and CN, wherein each R is independently H, alkyl, or aryl or heteroforms thereof.

A particularly preferred embodiment of a single $R^1$ is —$W_i$—$COX_jY$ wherein Y is $COR^2$ or an isostere thereof and $R^2$ is hydrogen or a noninterfering substituent, each of W and X is a spacer of 2-6 Å, and each of i and j is independently 0 or 1. Each of W and X is a spacer and may be, for example, optionally substituted alkyl, alkenyl, or alkynyl, each of i and j is 0 or 1. Preferably, W and X are unsubstituted. Preferably, j is 0 so that the two carbonyl groups are adjacent to each other. Preferably, also, i is 0 so that the proximal CO is adjacent the ring. However, compounds wherein the proximal CO is spaced from the ring can readily be prepared by selective reduction of an initially glyoxal substituted β ring. In the most preferred embodiments of the invention, the dotted line represents a double bond where the $CR^1$ in position 3- is that wherein $R^1$ is $W_iCOX_jY$, preferably $COCOR^2$, and $CR^1$ in position 2 is CH.

The noninterfering substituent represented by $R^2$, when $R^2$ is other than H, is a hydrocarbyl residue (1-20C) containing 0-5 heteroatoms selected from O, S and/or N or is an inorganic residue. Preferred are embodiments wherein $R^2$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, SR, OR, $NR_2$, OCOR, NRCOR, $NRCONR_2$, $NRSO_2R$, $NRSO_2NR_2$, $OCONR_2$, $CONR_2$, or $R_3Si$ wherein each $R^2$ is independently H, alkyl, alkenyl or aryl or the heteroatom-containing forms thereof, or wherein $R^2$ is OR, $NR_2$, SR, $NRCONR_2$, $OCONR_2$, or $NRSO_2NR_2$, wherein each R is independently H, alkyl, alkenyl or aryl or the heteroatom-containing forms thereof, and wherein two R attached to the same atom may form a 3-8 member ring and wherein said ring may further be substituted by alkyl, alkenyl, alkynyl, aryl, arylalkyl, heteroalkyl, heteroaryl, heteroarylalkyl, each optionally substituted, or by halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl or the heteroatom-containing forms thereof wherein two R attached to the same atom may form a 3-8 member ring, optionally substituted as above defined.

Other preferred embodiments of $R^2$ are H, heteroarylalkyl, $-NR_2$, heteroaryl, $-COOR$, $-NHRNR_2$, heteroaryl-COOR, heteroaryloxy, $-OR$, heteroaryl-$NR_2$, $-NROR$ and alkyl. Most preferably $R^2$ is isopropyl piperazinyl, methyl piperazinyl, dimethylamine, piperazinyl, isobutyl carboxylate, oxycarbonylethyl, benzimidazolyl, aminoethyldimethylamine, isobutyl carboxylate piperazinyl, oxypiperazinyl, ethylcarboxylate piperazinyl, methoxy, ethoxy, hydroxy, methyl, amine, aminoethyl pyrrolidinyl, aminopropanediol, piperidinyl, pyrrolidinyl-piperidinyl, or methyl piperidinyl, wherein each ring listed may optionally be substituted.

Isosteres of $COR^2$ as represented by Y are defined as follows.

The isosteres have varying lipophilicity and may contribute to enhanced metabolic stability. Thus, Y, as shown, may be replaced by the isosteres in Table 1.

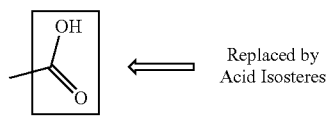

TABLE 1

Acid Isosteres

| Names of Groups | Chemical Structures | Substitution Groups (SG) |
|---|---|---|
| tetrazole | 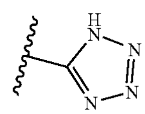 | n/a |
| 1,2,3-triazole | 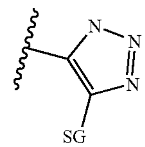 | H; $SCH_3$; $COCH_3$; Br; $SOCH_3$; $SO_2CH_3$; $NO_2$; $CF_3$; CN; COOMe |
| 1,2,4-triazole | 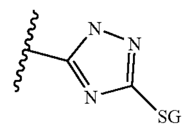 | H; $SCH_3$; $COCH_3$; Br; $SOCH_3$; $SO_2CH_3$; $NO_2$ |
| imidazole | 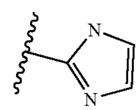 | H; $SCH_3$; $COCH_3$; Br; $SOCH_3$; $SO_2CH_3$; $NO_2$ |

Thus, isosteres include tetrazole, 1,2,3-triazole, 1,2,4-triazole and imidazole.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

The compounds of the invention may be synthesized by art-known methods. The following reaction schemes are illustrative:

Scheme 1

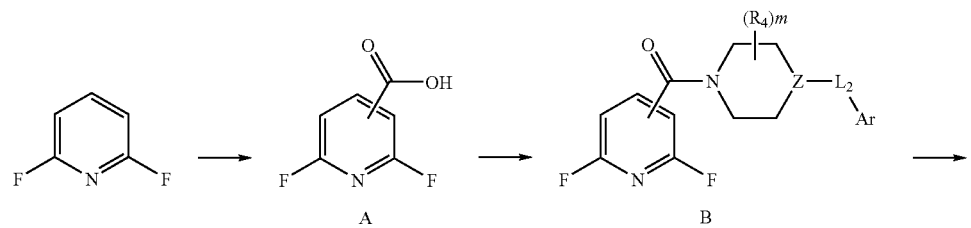

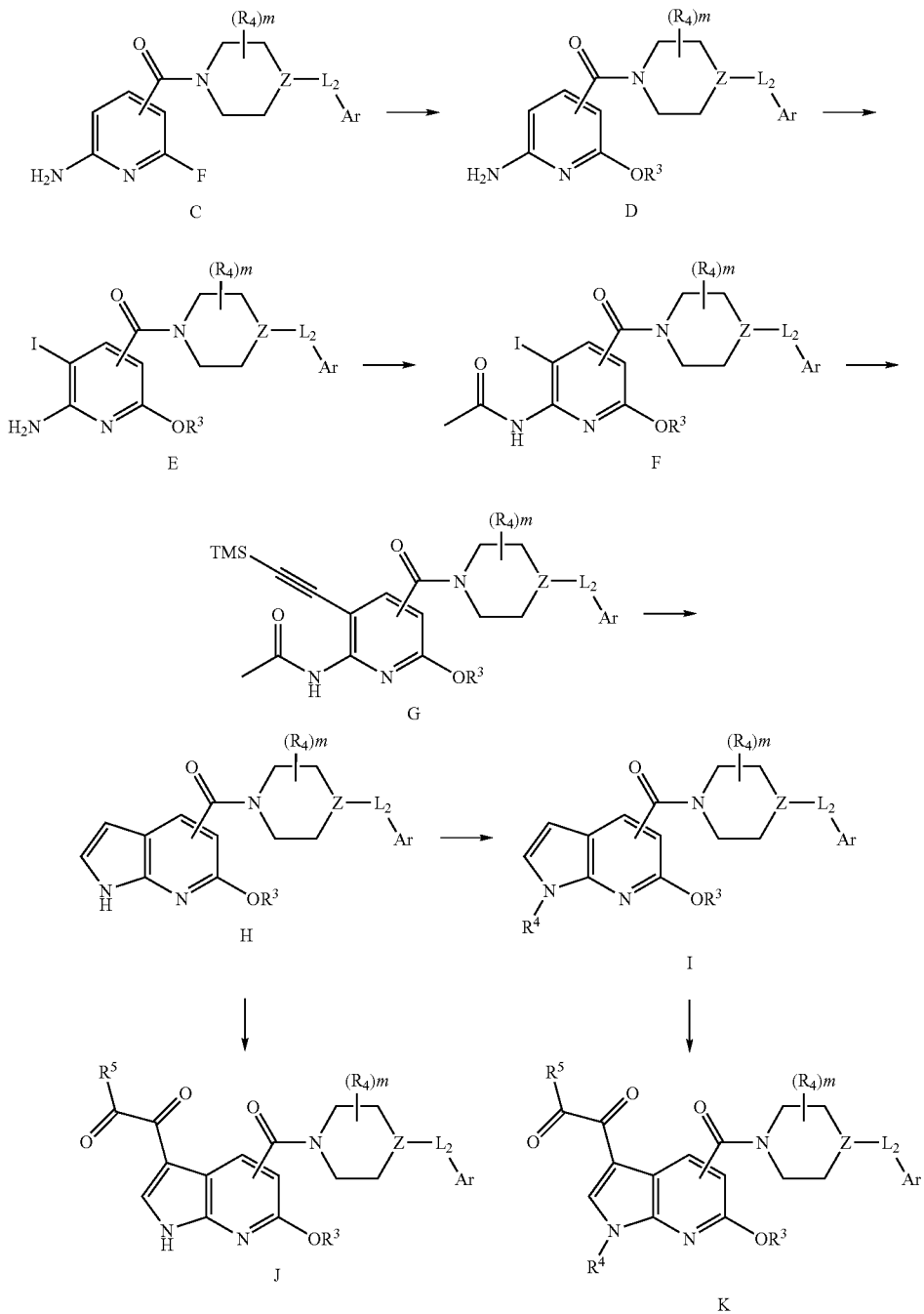

2,6-difluoropyridine can be converted to carboxylic acid A through treatment with a base such as lithium diisopropylamide at −78° C. in THF and then passing in a stream of dry $CO_2$. Carboxylic acid A can be converted to amide B through treatment with standard coupling reagents such as TBTU or EDCI and the appropriately substituted amine. B is dissolved in alcoholic solvent such as ethanol, methanol, or isopropanol whereupon ammonia gas is passed through the solution. The solution is sealed and heated until conversion to C is complete. Compound D is obtained by treating C with K-O$^t$Bu in the desired alcoholic solvent. Heating D in DMF with iodine and sodium periodate yields E. Acetyl chloride was added to a solution of E in THF and pyridine, yielding F. The trimethylsilylacetylene group was installed through treatment of F with trimethylsilyl acetylene in the presence of Pd(PPh$_3$)$_2$Cl$_2$, CuI, and an amine base. Cyclization to H is accomplished by refluxing a solution of G and tetrabutylammonium fluoride. At this point H can be functionalized by treatment with a base such as NaH, KOH, or LiHMDS followed by addition of an appropriate electrophile to give I. I is then treated with oxalyl chloride in DCM, DCE, or chloroform. To the resulting intermediate is then added the desired nucleophile to give K. H can be converted to J in a similar manner.

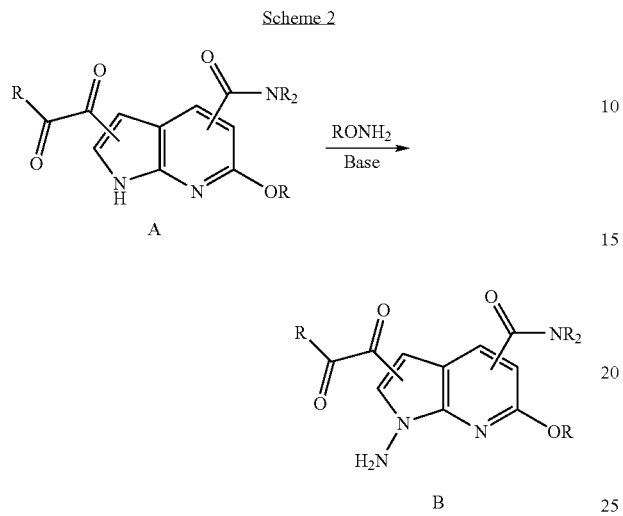

The indole nitrogen can be aminated with an N-amination reagent, such as those described in U.S. Provisional Patent Appln. 60/395,693 filed 11 Jul. 2002 entitled "Improved Reagents for N-Amination" and Tetrahedron Lett., vol. 23, No. 37, pages 3835-3836 1982, which are incorporated herein by reference, compound A reacts with an N-amination reactant to give the indole N-substituted compound B.

Examples of N-aminating reagents are $RONH_2$ where R is an aromatic that is appropriately substituted with electron withdrawing groups such as mono or di-nitro groups; diarylphosphinyl; or a substituted sulfonyl group. Examples include but are not limited to $(Ar)ONH_2$, $(Ar_2PO)ONH_2$, and $(ROSO_2)ONH_2$.

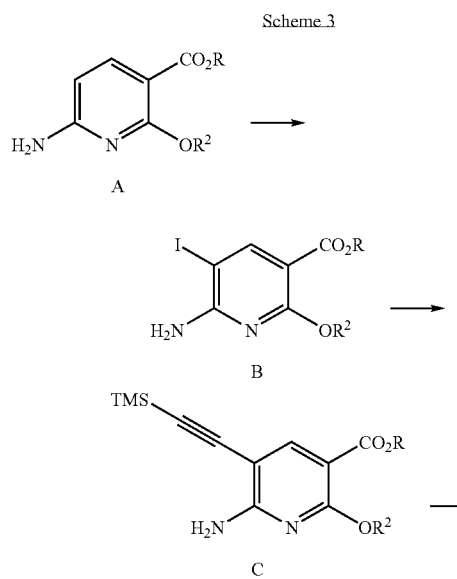

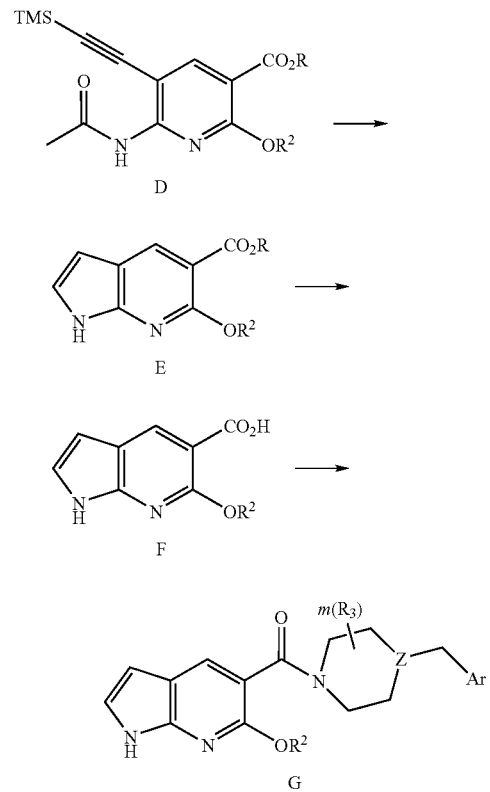

An alternate method to prepare 6-alkoxy-1H-pyrrolo[2,3-b]pyridine-5-carboxylic acid amides is provided in Scheme 3. Heating A in DMF with iodine and sodium periodate yields B. This can be coupled with trimethylsilylacetylene in the presence of $Pd(PPh_3)_2Cl_2$, CuI, and an amine base to provide C. Acetyl chloride is added to a solution of C in THF and pyridine to yield D. Cyclization is effected by heating D at reflux in the presence of tetrabutylammonium fluoride in THF, resulting in E. E can be converted to its corresponding carboxylic acid by treatment with aqueous base. Coupling of F with substituted amines under standard conditions using reagents like TBTU or EDCI results in compounds such as G.

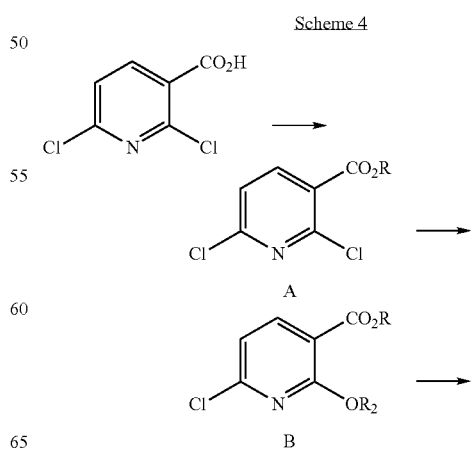

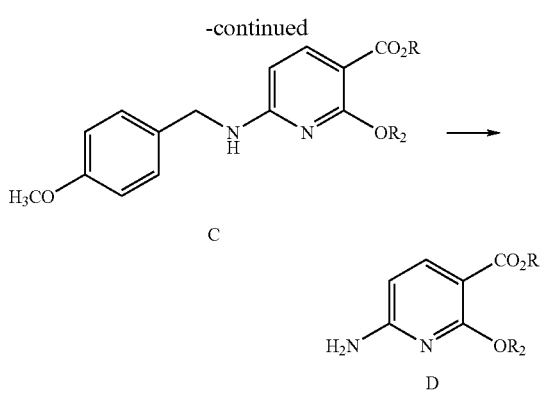

Various 6-Amino-2-alkoxy-nicotinic acid esters can be prepared from 2,6-dichloronicotinic acid, which is first converted into ester A by heating in the appropriate alcohol with catalytic amounts of acid, such as hydrochloric or sulfuric acid. Compound B can be prepared by treating A with sodium alkoxides in dichloromethane. By heating B and 4-methoxybenzylamine in the presence of an amine base in a polar aprotic solvent such as N-methylpyrrolidinone compound C is secured. C is converted into D by heating in warmed TFA until deprotection is complete.

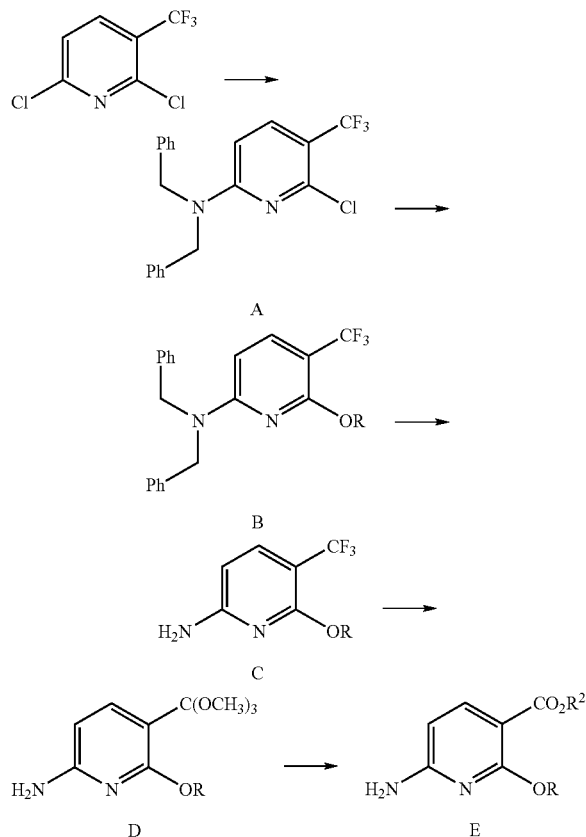

Another method can involve treatment of 2,6-dichloro-3-trifluromethylpyridine with dibenzylamine and an amine base in N-methylpyrrolidinone at elevated temperatures resulting in compound A. Heating A and an appropriate sodium alkoxide in DMF yields compound B. Removal of the diphenyl protecting group can be facilitated by treating a solution of compound B in wet methanol with palladium hydroxide on carbon under a pressure of hydrogen to give C. C can be converted to D by heating it in methanol in the presence of sodium methoxide. The ester, E, is obtained through treatment of D with dilute hydrochloric acid in the appropriate alcoholic solvent.

Assays for p38 α Kinase Inhibition

For each of the assay procedures described below, the TNF-α production correlates to the activity of p38-α kinase.

A. Human Whole Blood Assay for p38 Kinase Inhibition

Venous blood is collected from healthy male volunteers into a heparinized syringe and is used within 2 hours of collection. Test compounds are dissolved in 100% DMSO and 1 μl aliquots of drug concentrations ranging from 0 to 1 mM are dispensed into quadruplicate wells of a 24-well microtitre plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 μl of LPS (*E. coli* 0111:B4, Sigma Chemical Co., St. Louis, Mo.) is added to each well to a final concentration of 1 or 0.1 μg/ml for undiluted or 1:10 diluted whole blood, respectively. The incubation is continued for an additional 2 hours. The reaction is stopped by placing the microtitre plates in an ice bath and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.).

$IC_{50}$ values are calculated using the concentration of inhibitor that causes a 50% decrease as compared to a control.

B. Enriched Mononuclear Cell Assay for p38 Kinase Inhibition

The enriched mononuclear cell assay, the protocol of which is set forth below, begins with cryopreserved Human Peripheral Blood Mononuclear Cells (HPBMCs) (Clonetics Corp.) that are rinsed and resuspended in a warm mixture of cell growth media. The resuspended cells are then counted and seeded at $1\times10^6$ cells/well in a 24-well microtitre plate. The plates are then placed in an incubator for an hour to allow the cells to settle in each well.

After the cells have settled, the media is aspirated and new media containing 100 ng/ml of the cytokine stimulatory factor Lipopolysaccharide (LPS) and a test chemical compound is added to each well of the microtitre plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

LPS induced cytokine synthesis in HPBMCs

Cryopreserved HPBMC (cat#CC-2702 Clonetics Corp)

LGM-3 media (cat#CC-3212 Clonetics Corp)

LPS stock 10 µg/ml (Cat. No. L 2630 serotype 0111:B4 Sigma)
Human TNF-α ELISA (R&D Systems)
DNase I (10 mg/ml stock)
Preparation of cells.
LGM-3 media warmed to 37° C.
5 µl of DNase I stock added to 10 ml media.
Cells thawed rapidly and dispersed into above.
Centrifuge 200×g×10 min @ RT.
Pellet up in 10 ml sterile PBS.
Centrifuge 200×g×10 min @ RT.
Pellet resuspended in 10 ml LGM-3 then diluted to 50 ml with LGM-3.
Perform cell count.
Adjust to 1×E06 cells/well.
Seed 1 ml/well of a 24 well plate.
Place plate in incubator to plate down for 1 hour.
Preparation of incubation media.
LGM-3 containing 100 ng/ml LPS (e.g. 50 ml media plus 0.5 ml LPS stock)
Aliquot into 2 ml aliquots and add 1000×inhibitor dilutions.

Incubation

When cells have plated down, aspirate media away and overlay with 1 ml relevant incubation media. Return plate to incubator for 2 hours or 24 hours. Remove supernatants after incubation to a labeled tube and either perform TNF (or other) ELISA immediately or freeze for later assay.

$IC_{50}$ values are calculated using the concentration of inhibitor that causes a 50% decrease as compared to a control.

Administration and Use

The compounds of the invention are useful among other indications in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as Alzheimer's, coronary artery disease, congestive heart failure, cardiomyopathy, myocarditis, vasculitis, restenosis, such as occurs following coronary angioplasty, atherosclerosis, IBD, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), chronic pulmonary inflammatory disease, cystic fibrosis, silicosis, pulmonary sarcosis, sepsis, septic shock, endotoxic shock, Gram-negative sepsis, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone fracture healing, bone resorption diseases like osteoporosis, soft tissue damage, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y., et al., *J Biol Chem* (1996) 271:17920-17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S., et al., *Biochem Biophys Res Comm* (1997) 235: 533-538 and Stein, B., et al, *J Biol Chem* (1997) 272:19509-19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z., et al., *Biochem Biophys Res Comm* (1996) 228:334-340 and of p38-δ by Wang, X., et al., *J Biol Chem* (1997) 272:23668-23674 and by Kumar, S., et al, *Biochem Biophys Res Comm* (1997) 235:533-538. The data suggest that these two p38 isoforms (γ and ε) represent a unique subset of the MAPK family based on their tissue expression patterns, substrate utilization, response to direct and indirect stimuli, and susceptibility to kinase inhibitors.

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of p38 kinase can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implied above, although the compounds of the invention may be used in humans, they are also available for veterinary use in treating animal subjects.

The following examples are intended to illustrate but not to limit the invention, and to illustrate the use of the above Reaction Schemes.

EXAMPLE 1

Preparation of 1-{5-[4-(4-Fluoro-benzyl)-piperidine-1-carbonyl]-6-methoxy-1H-pyrrolo[2,3-b]pyridin-3-yl}-2-pyrrolidin-1-yl-ethane-1,2-dione

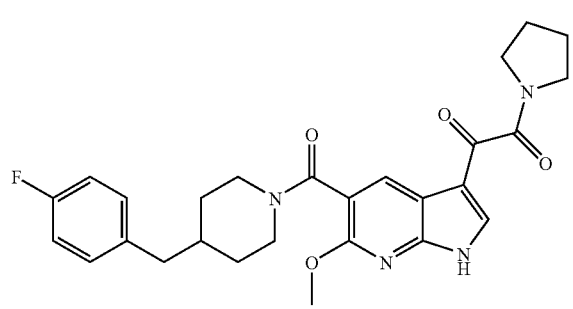

-continued
Step A

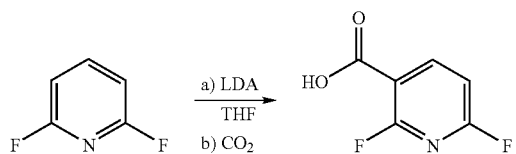

2,6-difluoropyridine-3-carboxylic acid (1) was prepared by using the method described by Rewcastle, G. W., et al., *J Med. Chem.* (1996) 39:1823-1835.

Step B

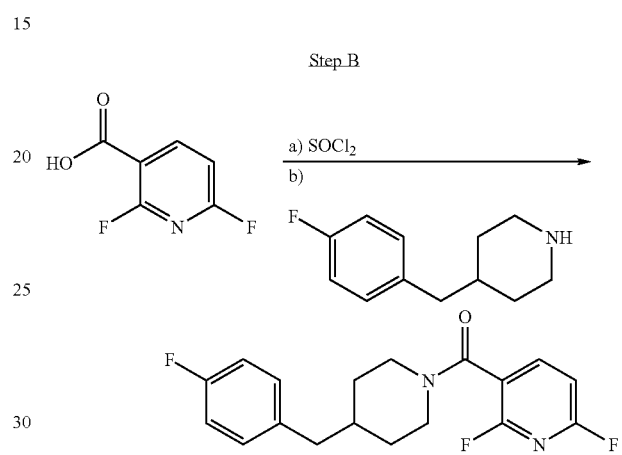

2,6-difluoropyridine-3-carboxylic acid (13.14 g) was suspended in dichloromethane (200 mL) and was cooled to 0° C. To this, under nitrogen atmosphere, was added thionyl chloride (30.14 mL, 413.2 mmol) dropwise. The ice-bath was removed and the mixture was refluxed for 3 h. The solvent was removed in vacuo. The product was taken up in dichloromethane (200 mL), stirred in an ice-bath and 4-fluorobenzylpiperidine hydrochloride (20.93 g, 91 mmol) was added followed by the dropwise addition of DIPEA (28.7 mL, 165.3 mmol). This was removed from the ice-bath and stirring continued for an additional 2 h at RT. The reaction mixture was poured into water and the organic layer was separated. The water layer was further extracted with dichloromethane (100 mL). The combined organic extracts was dried over sodium sulfate and evaporated. The residue was purified on a column of silica gel, eluting with ethyl acetate-hexane (20-50% ethyl acetate, gradient) to yield 23.58 g of the desired product. LCMS: 335, M+1

Step C

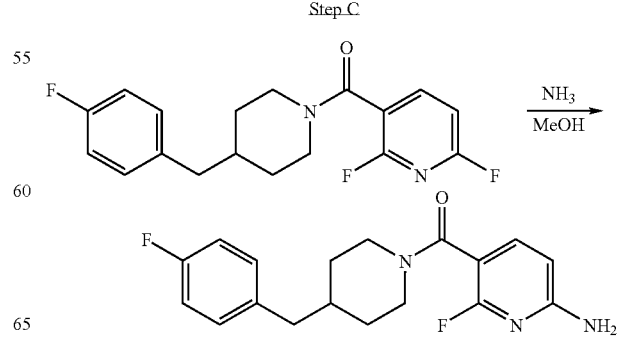

(2,6-Difluoro-pyridin-3-yl)-[4-(4-fluoro-benzyl)-piperidin-1-yl]-methanone (23.58 g) was dissolved in methanol (120 mL) in a sealed tube. This was cooled in a dry ice-acetone bath and a stream of ammonia gas was passed through the solution for about 5 min after which the reaction vessel was sealed. The mixture was heated in an oil bath at 60° C. for 20 h. The solvent was removed in vacuo and the residue was dissolved in dichloromethane and washed with water. The organic layer was dried over sodium sulfate and evaporated. The residue was purified on a column of silica gel eluting with ethyl acetate-hexane (50-70% ethyl acetate, gradient). The second major fraction contained the desired isomer (5.98 g, 25%). LCMS: 332, M +1

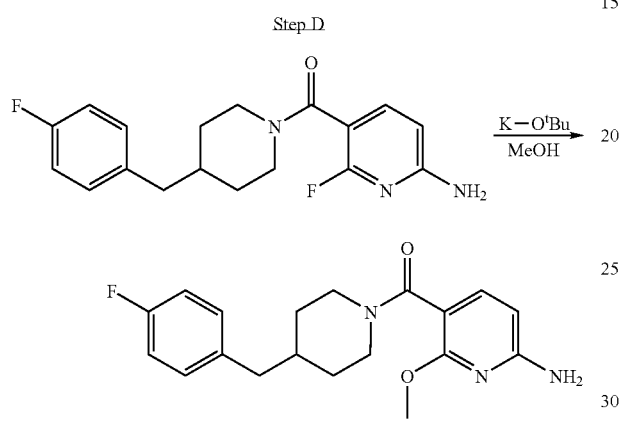

Step D (6-Amino-2-fluoro-pyridin-3-yl)-[4-(4-fluoro-benzyl)-piperidin-1-yl]-methanone (5.86 g, 17.7 mmol) was taken in methanol (60 mL). Potassium-t-butoxide (9.9 g, 85.5 mmol) was added and the mixture was refluxed for 6 h. The methanol was removed under reduced pressure and the residue was extracted from water with ethyl acetate. After drying over sodium sulfate it was evaporated and the residue was purified on a column of silica gel with ethyl acetate-hexane (50-70%, gradient) as eluent to yield 5.46 g (90%) of the desired product. LCMS: 344, M+1

Step E

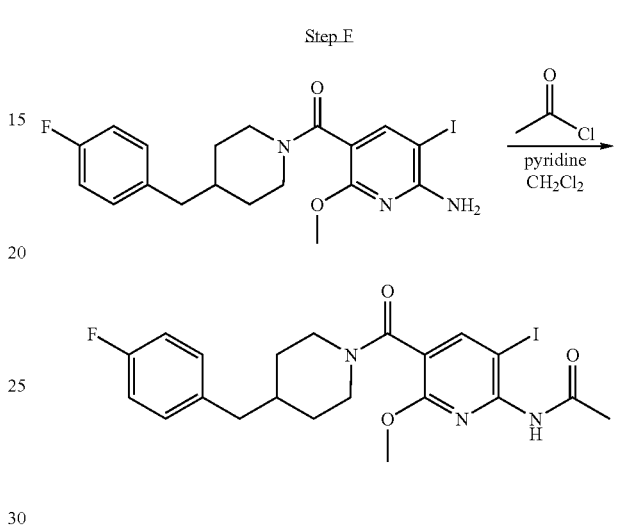

(6-Amino-2-methoxy-pyridin-3-yl)-[4-(4-fluoro-benzyl)-piperidin-1-yl]-methanone (5.44 g, 15.86 mmol) of was dissolved in dry DMF (70 mL). Iodine (3.23 g, 12.70 mmol, 0.8 eq.) was added followed by sodium periodate (1.36 g, 6.34 mmol, 0.4 eq.). The mixture was heated at 50° C. under nitrogen with stirring for 4.5 h. It was then poured into water and extracted with ethyl acetate (3×100 mL). The combined extract was washed with dilute sodium thiosulfate solution to remove the excess iodine. The ethyl acetate extract was dried over sodium sulfate and evaporated. The residue was purified on a column of silica gel eluting with ethyl acetate-hexane (20-40% ethyl acetate, gradient) to yield 6.46 g (86.8%) of the desired product. LCMS: 470, M+1

Step F (6-Amino-5-iodo-2-methoxy-pyridin-3-yl)-[4-(4-fluoro-benzyl)-piperidin-1-yl]-methanone (6.46 g, 13.8 mmol) was taken in dry THF (100 mL). Pyridine (1.7 mL, 20.7 mmol) was added and the mixture was cooled in an ice-bath. To this mixture was added dropwise under nitrogen acetyl chloride (1.3 mL, 18 mmol) in dry THF (10 mL). After the addition, the ice-bath was removed and stirring continued at RT for another 20 h. The solvent was removed under reduced pressure and the residue was taken up in water and extracted with dichloromethane (3×100 mL). The combined extracts were dried over sodium sulfate and evaporated. The residue was purified on a column of silica gel eluting with ethyl acetate-hexane (40-70% ethyl acetate, gradient) to yield 4.91 g (69.6%) of the desired product. LCMS: 511.

Step G

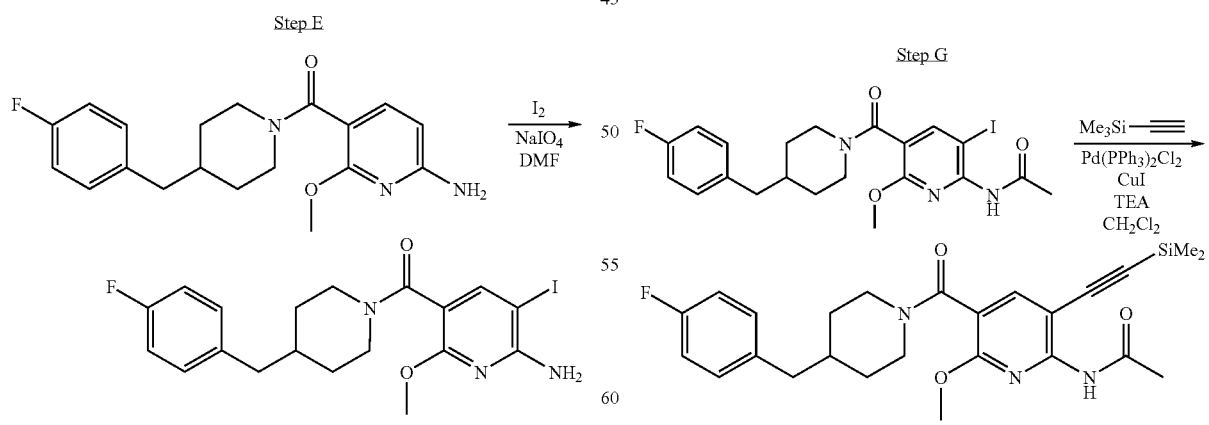

N-{5-[4-(4-Fluoro-benzyl)-piperidine-1-carbonyl]-3-iodo-6-methoxy-pyridin-2yl}-acetamide (4.9 g, 9.59 mmol) was taken in dry dichloromethane (100 mL) and TEA (1.6 mL, 11.51 mmol) was added. The mixture was cooled in an ice-bath and Pd(PPh$_3$)$_2$Cl$_2$ (35 mg, 0.05 mmol) and CuI (19 mg, 0.10 mmol) were added. To the stirred mixture was then added dropwise trimethylsilyl acetylene (1.49 mL, 10.55 mmol). The reaction mixture was removed from ice-bath and stirring continued for 20 h at RT. The reaction mixture was filtered to remove the solids and the filtrate was evaporated to dryness. The residue was purified on a column of silica gel eluting it with ethyl acetate-hexane (20-50% ethyl acetate, gradient), to yield 4.24 g (92%) of the desired compound. LCMS: 481.

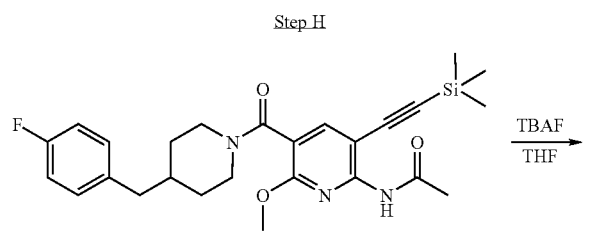

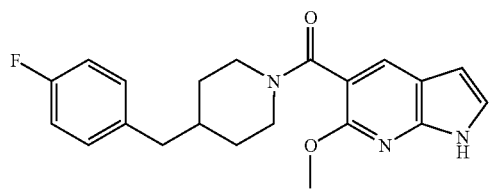

N-{5-[4-(4-Fluoro-benzyl)-piperidine-1-carbonyl]-6-methoxy-3-trimethylsilanylethynyl-pyridin-2-yl}-acetamide (4.24 g, 8.8 mmol) was dissolved in dry THF (50 mL). Tetrabutylammonium fluoride (1M solution in THF, 17.6 mL, 17.6 mmol) was added and the mixture refluxed with stirring for 3 h. The solvent was removed under reduced pressure and the residue was taken in water and extracted with dichloromethane (3×75 mL). The combined extracts were dried over sodium sulfate and evaporated. The residue was purified in a column of silica gel, eluting it with ethyl acetate-hexane (20-50% ethyl acetate, gradient) to yield 2.7 g of the desired product. LCMS: 368, M+1

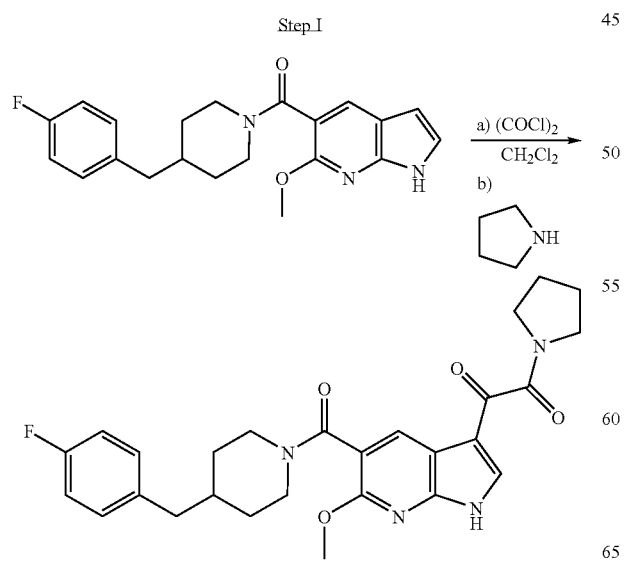

[4-(4-Fluoro-benzyl)-piperidin-1-yl]-(6-methoxy-1H-pyrrolo[2,3-b]pyridin-5-yl)-methanone (368 mg, 1 mmol) was dissolved in dry dichloromethane (5 mL). It was cooled in an ice-bath and oxalyl chloride (4.5 mL, 2 M solution in dichloromethane) was added. The mixture was stirred for 1 h at 0° C. and for another 4 h at room temperature. It was evaporated to dryness, redissolved in dichloromethane and treated with pyrrolidine (3 mmol). After stirring for 30 min, water was added and the product was extracted with dichloromethane (3×25 mL). The combined extracts were dried over sodium sulfate. After evaporation of the solvent, the product was purified via radial chromatography using chloroform-methanol (0-3% methanol) to yield 340 mg of the desired product. LCMS: 493, M+1.

EXAMPLE 2

Preparation of 2-{5-[4-(4-Fluoro-benzyl)-piperidine-1-carbonyl]-6-methoxy-1H-pyrrolo[2,3-b]pyridin-3-yl}-N,N-dimethyl-2-oxo-acetamide

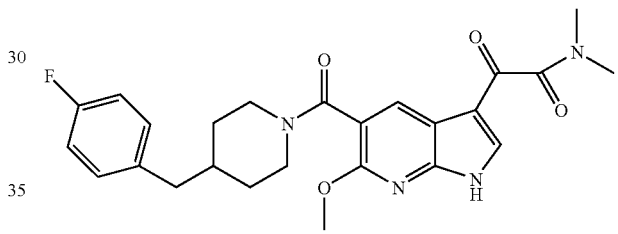

Prepared using the same method described in Example 1, Step I using [4-(4-Fluoro-benzyl)-piperidin-1-yl]-(6-methoxy-1H-pyrrolo[2,3-b]pyridin-5-yl)-methanone and substituting dimethylamine for pyrrolidine. LCMS: 467, M+1.

EXAMPLE 3

Preparation of 2-{5-[4-(4-Fluoro-benzyl)-piperidine-1-carbonyl]-6-methoxy-1H-pyrrolo[2,3-b]pyridin-3-yl}-N-methyl-2-oxo-acetamide

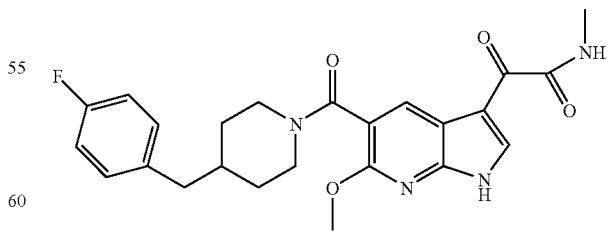

Prepared using the same method described in Example 1, Step I using [4-(4-Fluoro-benzyl)-piperidin-1-yl]-(6-methoxy-1H-pyrrolo[2,3-b]pyridin-5-yl)-methanone and substituting methylamine for pyrrolidine. LCMS: 453, M+1.

EXAMPLE 4

Preparation of 1-{5-[4-(4-Fluoro-benzyl)-piperidine-1-carbonyl]-6-methoxy-1H-pyrrolo[2,3-b]pyridin-3-yl}-2-(3-hydroxy-pyrrolidin-1-yl)-ethane-1,2-dione

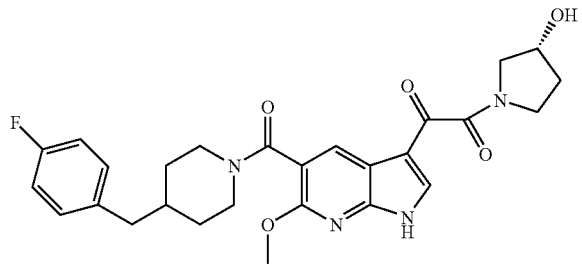

Prepared using the same method described in Example 1, Step I using [4-(4-Fluoro-benzyl)-piperidin-1-yl]-(6-methoxy-1H-pyrrolo[2,3-b]pyridin-5-yl)-methanone and substituting 3-hydroxypyrrolidine for pyrrolidine. LCMS: 509, M+1.

EXAMPLE 5

Preparation of 2-{5-[4-(4-Fluoro-benzyl)-piperidine-1-carbonyl]-6-methoxy-1H-pyrrolo[2,3-b]pyridin-3-yl}-N-(2-hydroxy-ethyl)-2-oxo-acetamide

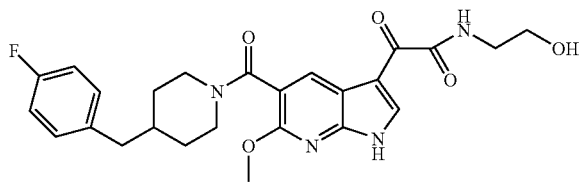

Prepared using the same method described in Example 1, Step I using [4-(4-Fluoro-benzyl)-piperidin-1-yl]-(6-methoxy-1H-pyrrolo[2,3-b]pyridin-5-yl)-methanone and substituting ethanolamine for pyrrolidine. LCMS: 483, M+1.

EXAMPLE 6

Preparation of N-Ethyl-2-{5-[4-(4-fluoro-benzyl)-piperidine-1-carbonyl]-6-methoxy-1H-pyrrolo[2,3-b]pyridin-3-yl}-N-methyl-2-oxo-acetamide

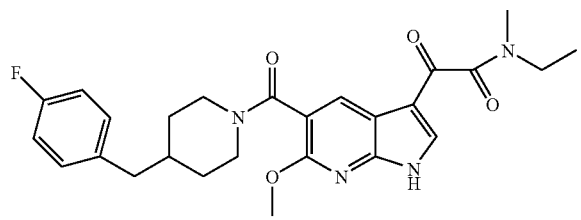

Prepared using the same method described in Example 1, Step I using [4-(4-Fluoro-benzyl)-piperidin-1-yl]-(6-methoxy-1H-pyrrolo[2,3-b]pyridin-5-yl)-methanone and substituting methylethylamine for pyrrolidine. LCMS: 481, M+1.

EXAMPLE 7

Preparation of 2-{5-[4-(4-Fluoro-benzyl)-piperidine-1-carbonyl]-6-methoxy-1H-pyrrolo[2,3-b]pyridin-3-yl}-2-oxo-N-pyrrolidin-1-yl-acetamide

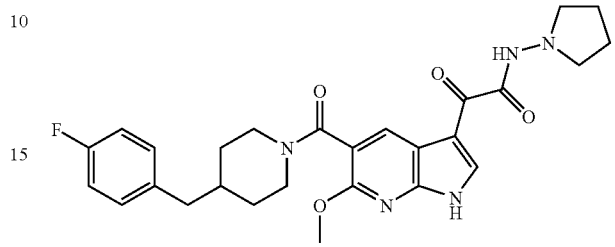

This compound was prepared according to the procedure in Example 1, Step I using pyrrolidin-1-ylaamine in place of pyrrolidine. M+H$^+$(508).

EXAMPLE 8

Preparation of 2-{5-[4-(4-Fluoro-benzyl)-piperidine-1-carbonyl]-6-methoxy-1H-pyrrolo[2,3-b]pyridin-3-yl}-2-oxo-acetamide

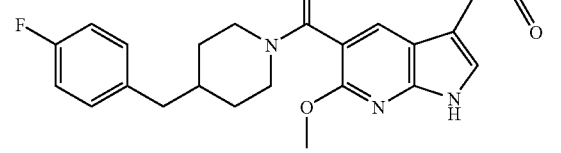

Prepared according to the procedure in Example 1, Step I using ammonia in place of pyrrolidine. M+H$^+$(439).

EXAMPLE 9

Preparation of N-Ethyl-2-{5-[4-(4-fluoro-benzyl)-piperidine-1-carbonyl]-6-methoxy-1H-pyrrolo[2,3-b]pyridin-3-yl}-2-oxo-acetamide

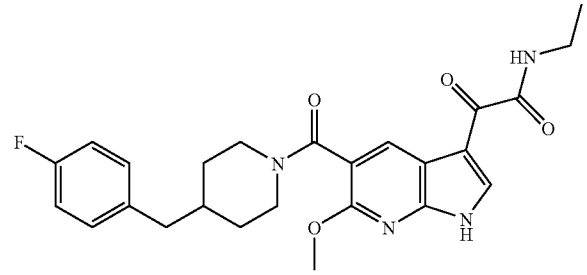

Prepared according to the procedure in Example 1, Step I using ethylamine in place of pyrrolidine. M+H$^+$(467).

EXAMPLE 10

Preparation of 1-{5-[4-(4-Fluoro-benzyl)-piperidine-1-carbonyl]-6-methoxy-1-methyl-1H-pyrrolo[2,3-b]pyridin-3-yl}-2-pyrrolidin-1-yl-ethane-1,2-dione

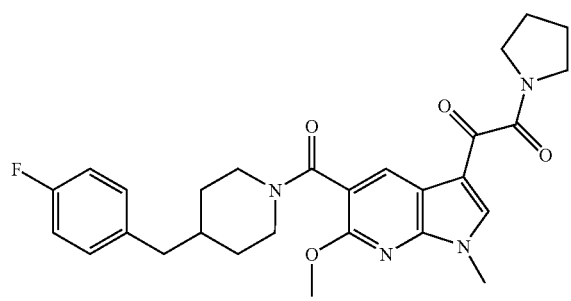

Step A

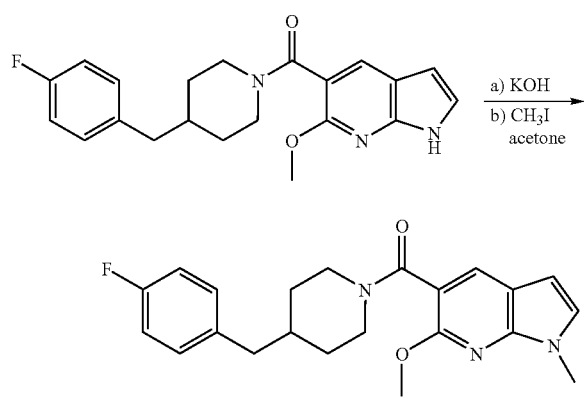

To a solution of [4-(4-Fluoro-benzyl)-piperidin-1-yl]-(6-methoxy-1H-pyrrolo[2,3-b]pyridin-5-yl)-methanone (100 mg, 0.27 mmol) and ground KOH (76 mg, 1.36 mmol) in anhydrous acetone (15 mL) was added iodomethane (96 mg, 0.675 mmol) at 0° C. The reaction mixture was warmed to RT slowly and stirred overnight. The solvent was removed, and the residue was treated with water and extracted with EtOAc. The combined organic layer was washed with brine, dried and concentrated. The residue was purified by chromatography on silica gel eluting with EtOAc:hexane (1:1) to give the desired product 100 mg (98% yield) as a white solid. M+H⁺ (382).

Step B

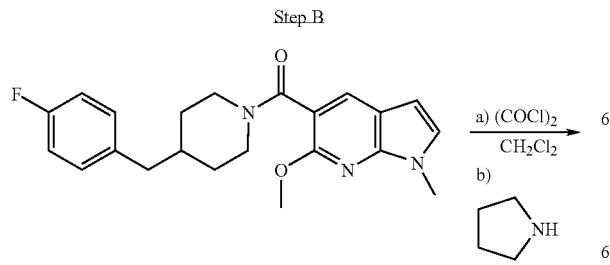

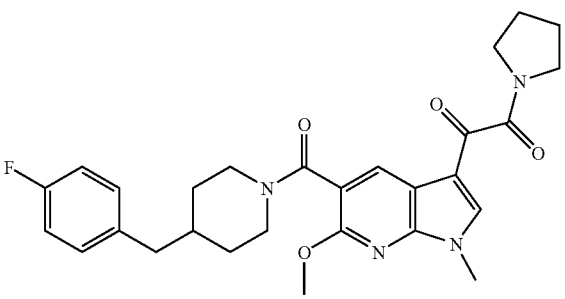

To a solution of [4-(4-Fluoro-benzyl)-piperidin-1-yl]-(6-methoxy-1-methyl-1H-pyrrolo[2,3-b]pyridin-5-yl)-methanone (100 mg, 0.26 mmol) in anhydrous CH$_2$Cl$_2$ (15 mL) was added oxalyl chloride (0.52 mL, 1.05 mmol, 2 M in CH$_2$Cl$_2$) at RT. The reaction mixture was stirred for 4 h. The reaction mixture was concentrated under reduced pressure. The residue was dried under vacuum for 1 h and dissolved in CH$_2$Cl$_2$ (15 mL). An excess amount of pyrrolidine (74 mg, 1.04 mmol) was added to the reaction mixture. After stirring for 1 h, the reaction mixture was treated with water. The organic layer was separated and washed with brine, dried and concentrated. The residue was purified by chromatography on silica gel eluting with CH$_2$Cl$_2$:MeOH (95:5) to give the desired product (70 mg) in 53% yield as a white solid. M+H⁺ (507).

EXAMPLE 11

Additional Compounds

The synthesis of the following compounds can be carried out in a manner similar to the procedure described in Example 10.

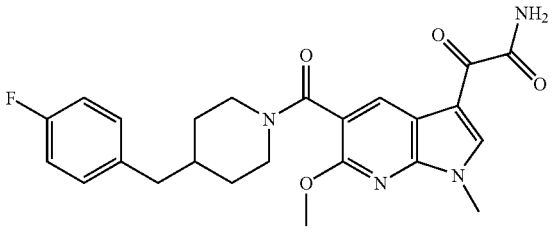

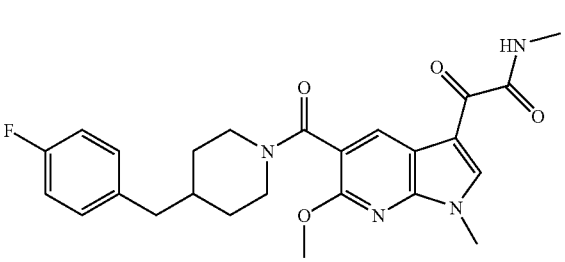

-continued

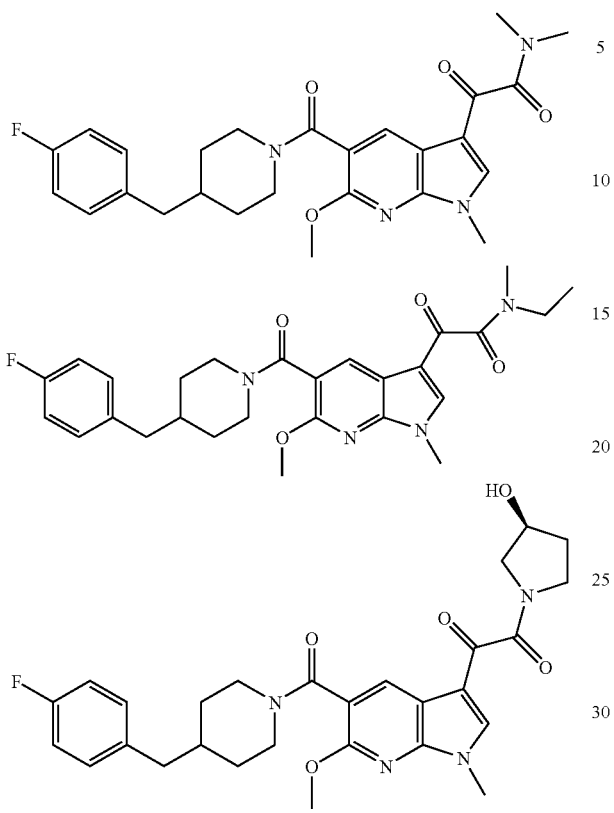

EXAMPLE 12

Preparation of 1-{5-[4-(4-Fluoro-benzyl)-piperidine-1-carbonyl]-6-methoxy-1-methoxymethyl-1H-pyrrolo[2,3-b]pyridin-3-yl}-2-pyrrolidin-1-yl-ethane-1,2-dione -continued

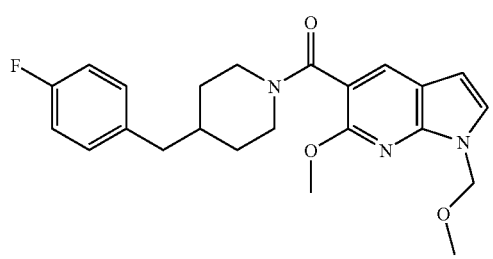

To a solution of [4-(4-Fluoro-benzyl)-piperidin-1-yl]-(6-methoxy-1H-pyrrolo[2,3-b]pyridin-5-yl)-methanone (150 mg, 0.41 mmol) and ground KOH (114 mg, 2 mmol) in anhydrous acetone (15 mL) was added MOM chloride (82 mg, 1 mmol) at 0° C. The reaction mixture was warmed to RT slowly and stirred overnight. The solvent was removed, and the residue was treated with water and extracted with EtOAc. The combined organic layer was washed with brine, dried and concentrated. The residue was purified by chromatography on silica gel eluting with EtOAc:hexane (1:1) to give the desired product 130 mg (77% yield) as a white solid. M+H$^+$ (411).

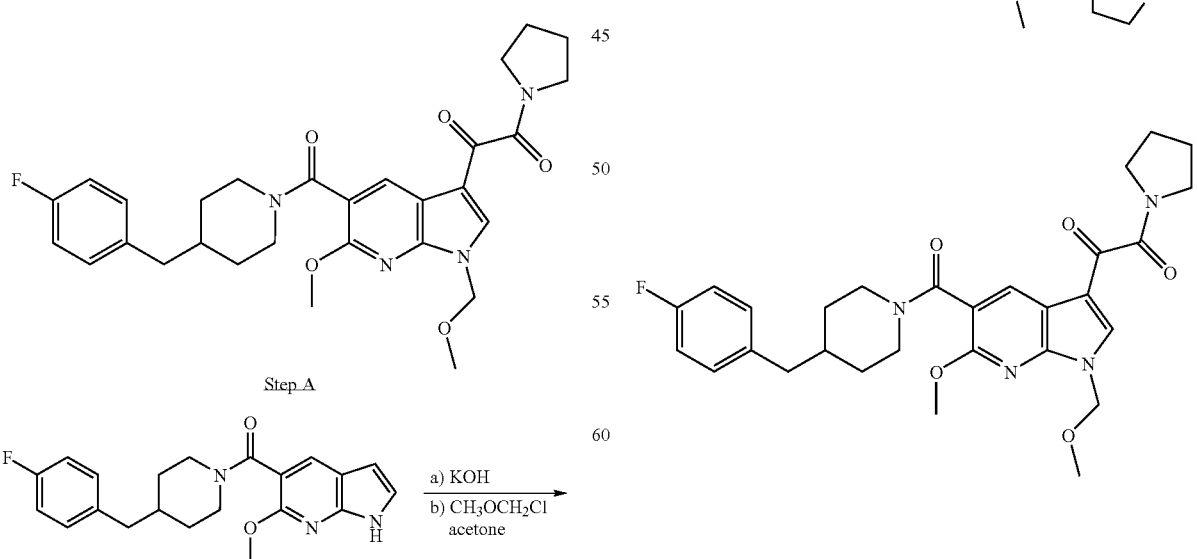

This compound was prepared according to the procedure in Example 10, Step B. M+H$^+$(537).

EXAMPLE 13

Additional Compounds

The synthesis of the following compounds can be carried out in a manner similar to re described in Example 12.

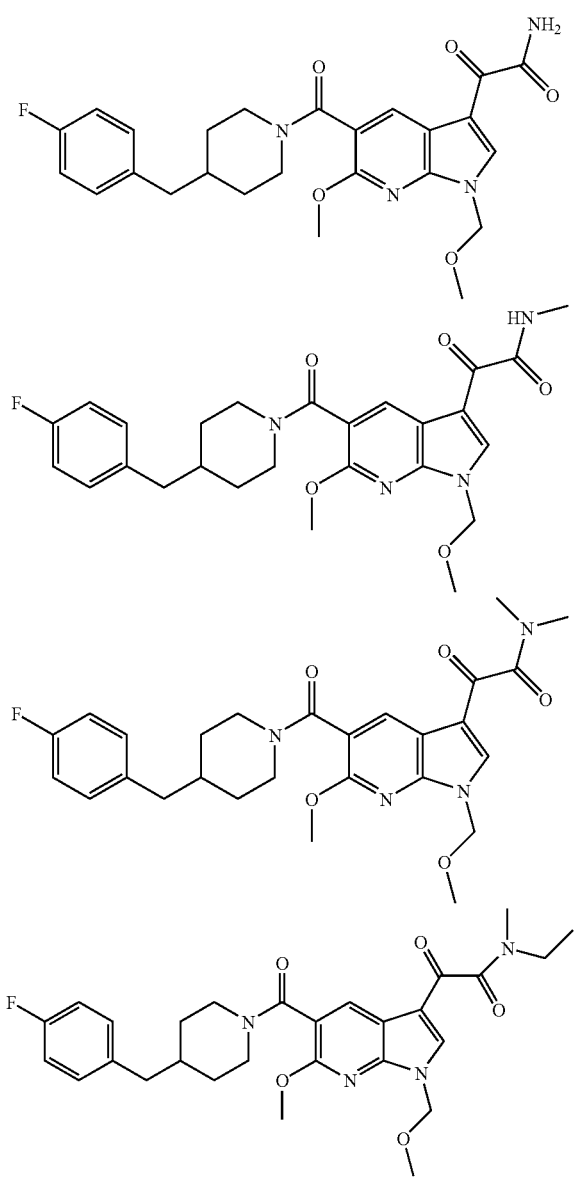

EXAMPLE 14

Preparatioin of 1-{1-Amino-5-[4-(4-fluoro-benzyl)-piperidine-1-carbonyl]-6-methoxy-1H-pyrrolo[2,3-b]pyridin-3-yl}-2-porrlidin-1-yl-ethane-1,2-dione

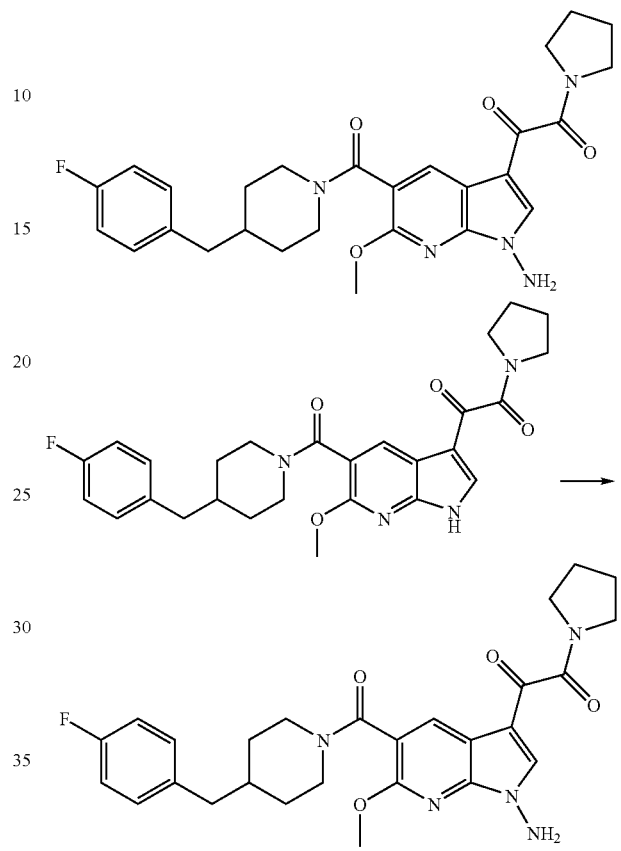

To a solution of 1-{5-[4-(4-Fluoro-benzyl)-piperidine-1-carbonyl]-6-methoxy-1H-pyrrolo[2,3-b]pyridin-3-yl}-2-pyrrolidin-1-yl-ethane-1,2-dione (76 mg, 0.154 mmol) in DMF (10 mL) was added 2,5-dinitro benzohydroxylamine (40 mg, 0.2 mmol) and $K_2CO_3$ (43 mg, 0.308 mmol). The reaction mixture was stirred at RT for 6 h, then treated with water (20 mL). The resulting mixture was extracted with EtOAc, washed with brine, dried ($Na_2SO_4$) and concentrated. The residue was purified by chromatography on silica gel eluting with 2% MeOH in $CH_2Cl_2$ to give 57 mg (73%) of the desired product as a white solid. M+H$^+$(508).

EXAMPLE 15

Additional Compounds

The synthesis of the following compounds can be carried out in a manner similar to the procedure described in Example 14.

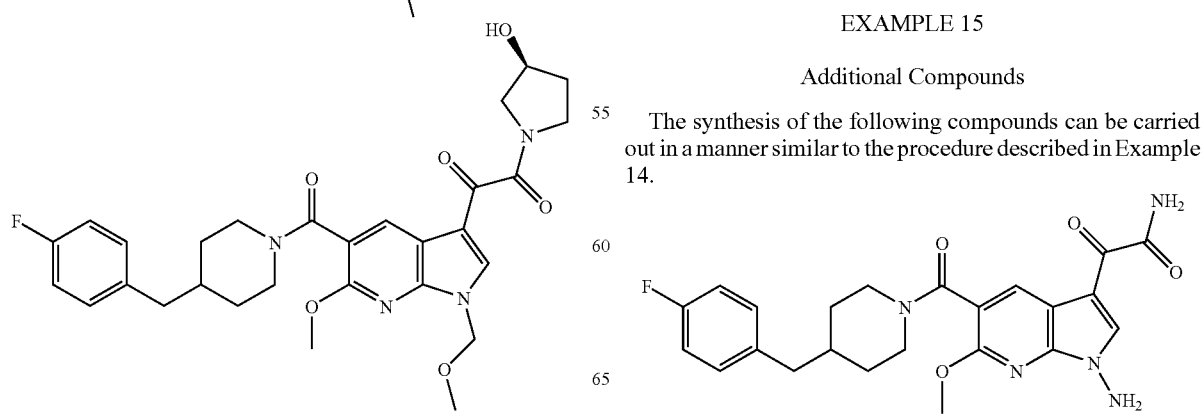

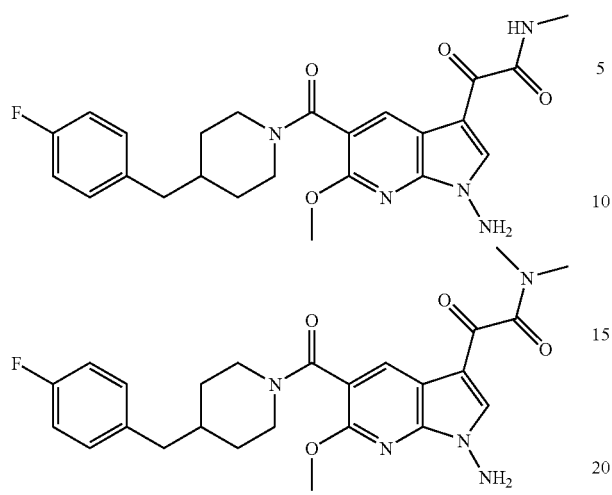

EXAMPLE 16

Preparation of 1-{5-[4-(4-Fluoro-benzyl)-2R,5S-dimethyl-piperazine-1-carbonyl]-6-methoxy-1H-pyrrolo[2,3-b]pyridin-3-yl}-2-pyrrolidin-1-yl-ethane-1,2-dione

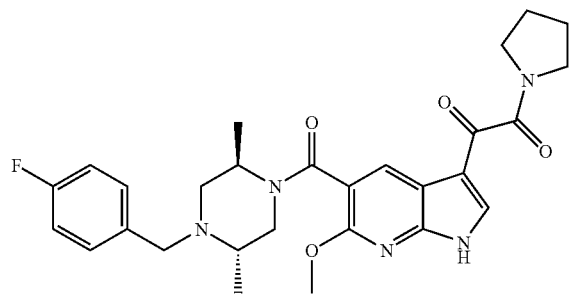

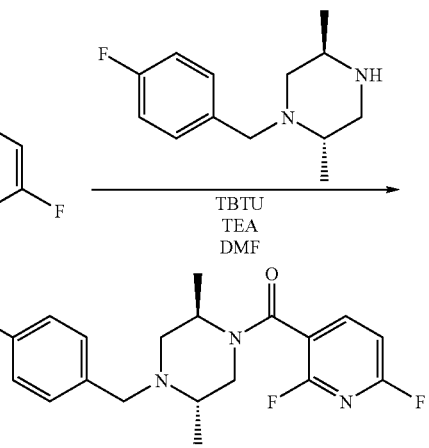

To a solution of 2,6-difluoropyridine-3-carboxylic acid (4.16 g, 26.2 mmol) and 4-fluorobenzyl-2S,5R-dimethyl piperazine (4.8 g, 21.8 mmol) in dimethylformamide was added TBTU (10.5 g, 32.7 nmol) followed by triethylamine (9 mL, 65.4 mmol). The reaction mixture was stirred overnight at RT and then poured into ice water. The precipitate formed was filtered and dissolved in dichloromethane. Two scoops of silica gel were added to the solution. The mixture was concentrate under reduced pressure. The residue was dry loaded on silica gel column eluting with EtOAc:hexane (4:6) to give 4 g (42%) of the desired product as a white solid. M+H$^+$(364).

Ammonium gas (2 mL) was condensed and added to a cold solution of (2,6-Difluoro-pyridin-3-yl)-[4-(4-fluoro-benzyl)-2R,5S-dimethyl-piperazin-1-yl]-methanone (2 g, 8.26 mmol) in methanol (20 mL) in a Parr pressure reaction vessel at −78° C. The reaction vessel was sealed immediately and warmed to RT. The reaction mixture was heated at 60° C. overnight and cooled to −78° C. The reaction vessel was opened and the reaction mixture was then concentrated. The residue was purified by chromatography on silica gel eluting with EtOAc:hexane (1:1) then EtOAc:hexane (4:1) to give 750 mg (25%) of the undesired regioisomer, followed by 800 mg (27%) of the desired product as a white solid. M+H$^+$(361).

Step C

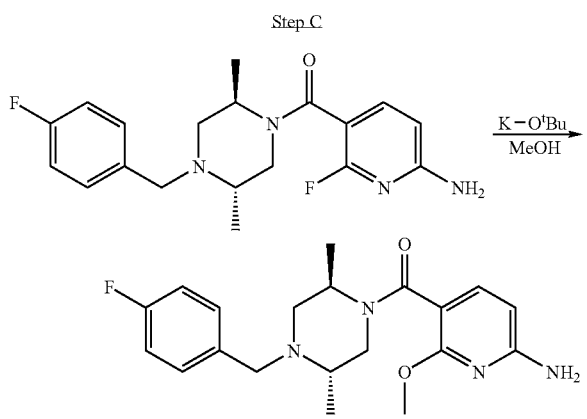

Potassium tert-butoxide (2.5 g, 22.2 mmol) was added to a solution of (6-Amino-2-fluoro-pyridin-3-yl)-[4-(4-fluoro-benzyl)-2R,5S-dimethyl-piperazin-1-yl]-methanone (1.6 g 4.44 mmol) in anhydrous methanol (10 mL) at RT. The reaction mixture was refluxed overnight and then concentrated. The residue was treated with water and the resulting mixture was extracted with EtOAc. The combined organic extracts were washed with brine, dried and concentrated. The residue was purified by chromatography on silica gel eluting with EtOAc:hexane (2:1) to give 1.3 g (79%) of the desired product as a white foam. M+H$^+$(361).

Step D

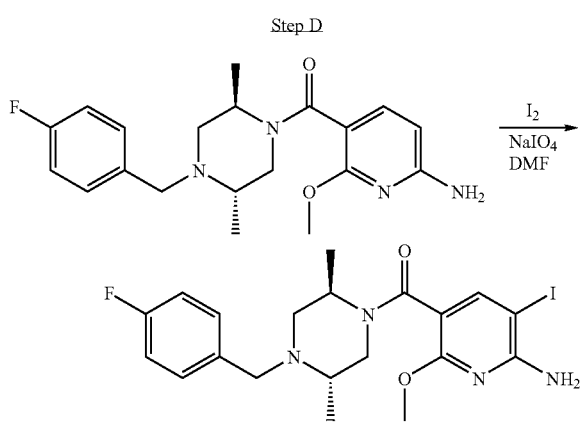

Method 1: To a solution of (6-Amino-2-methoxy-pyridin-3-yl)-[4-(4-fluoro-benzyl)-2R,5S-dimethyl-piperazin-1-yl]-methanone (800 mg, 2.15 mmol) in anhydrous DMF (20 mL) was added iodine (557 mg, 2.15 mmol) and sodium periodate (238 mg, 1.11 mmol). The reaction mixture was heated up at 50° C. overnight. The reaction mixture was poured into ice water and a solution of sodium thiosulfate (10%) was added to destroy the excess iodine. The precipitate formed was filtered. The crude product was purified by chromatography on silica gel (pre-treated with Et$_3$N) eluting with EtOAc:hexane (1:2) to give 522 mg (52%) of the desired product as a white foam. M+H$^+$(499).

Method 2: Benzyltrimethylammonium dichloroiodate (1.46 g, 4.2 mmol) was added to a solution of (6-Amino-2-methoxy-pyridin-3-yl)-[4-(4-fluoro-benzyl)-2R,5S-dimethyl-piperazin-1-yl]-methanone (1.2 g, 3.2 mmol) and calcium carbonate (1.1 g, 11 mmol) in anhydrous dichloromethane (25 mL) at RT. The reaction mixture was stirred overnight. The organic layer was washed with water and 10% sodium thiosulfate, dried and concentrated. The residue was purified by chromatography on silica gel eluting with EtOAc:hexane (1:2) to give 910 mg (57%) of the desired product as a white foam. M+H$^+$(499).

Step E

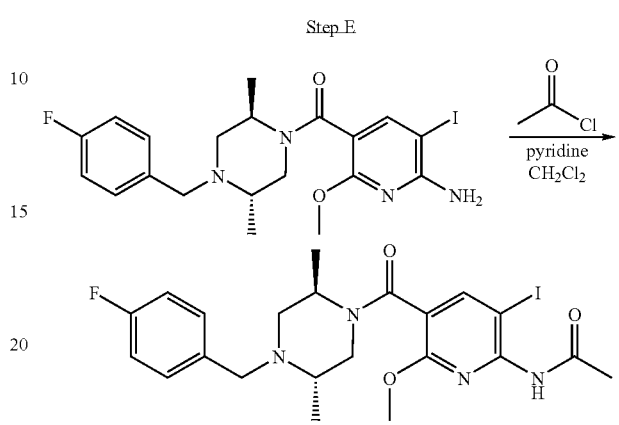

Acetyl chloride (48 mg, 0.62 mmol) was added to a solution of (6-Amino-5-iodo-2-methoxy-pyridin-3-yl)-[4-(4-fluoro-benzyl)-2R,5S-dimethyl-piperazin-1-yl]-methanone (235 mg, 0.47 mmol) and pyridine (0.057 mL, 0.7 mmol) in dichloromethane (10 mL) at RT. The reaction mixture was stirred at RT overnight, and then treated with water. The organic layer was separated, dried and concentrated. The residue was purified by chromatography on silica gel eluting with EtOAc:hexane (1:1) to give 150 mg (59%) of the desired product as a colorless oil. M+H$^+$(541).

Step F

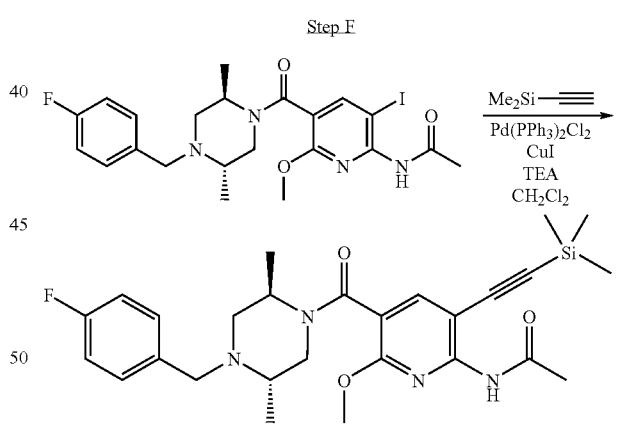

To a solution of N-{5-[4-(4-Fluoro-benzyl)-2R,5S-dimethyl-piperazine-1-carbonyl]-3-iodo-6-methoxy-pyridin-2-yl}-acetamide (100 mg, 0.185 mmol), palladium bis(triphenylphosphane) dichloride (65 mg, 0.09 mmol), copper iodide (2 mg, 0.01 mmol) in anhydrous dichloromethane (5 mL) was added trimethlsilyacetylene (18 mg, 0.185 mmol) dropwise at 0° C. The reaction mixture was stirred at RT overnight, filtered through a plug of celite and concentrated. The residue was taken up into ethyl acetate, and washed with water and brine, dried and concentrated. The residue was purified by chromatography on silica gel eluting with EtOAc:hexane (1:1) to give 90 mg (96%) of the desired product. M+H$^+$(511).

Step G

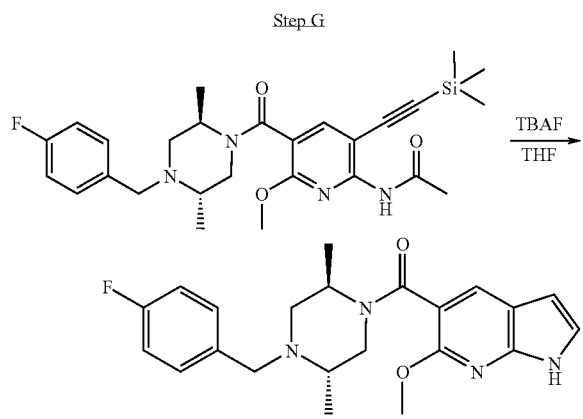

A mixture of N-{5-[4-(4-Fluoro-benzyl)-2R,5S-dimethyl-piperazine-1-carbonyl]-6-methoxy-3-trimethylsilanylethynyl-pyridin-2-yl}-acetamide (350 mg, 0.686 mmol) and tetrabutylammonium fluoride (1.37 mL, 1.37 mmol, 1.0 M in THF) in anhydrous THF was heated at reflux for 4 h. The reaction mixture was concentrated and the residue was taken up into ethyl acetate. The organic layer was washed with water, brine, dried and concentrated. The residue was purified by chromatography on silica gel eluting with EtOAc:hexane (4:6) to give 170 mg (63%) of the desired product as a colorless oil. M+H$^+$(397).

Step H

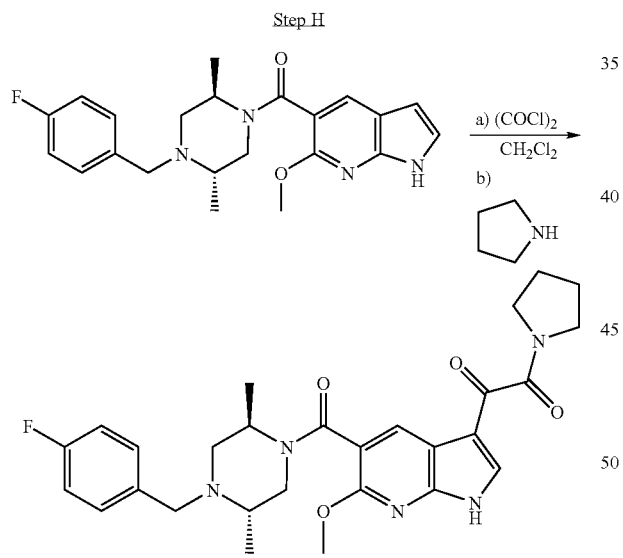

To a solution of [4-(4-Fluoro-benzyl)-2R,5S-dimethyl-piperazin-1-yl]-(6-methoxy-1H-pyrrolo[2,3-b]pyridin-5-yl)-methanone (170 mg, 0.43 mmol) in anhydrous CH$_2$Cl$_2$ (15 mL) was added oxalyl chloride (0.86 mL, 1.72 mmol, 2 M in CH$_2$Cl$_2$) at RT. The reaction mixture was stirred overnight. The reaction mixture was concentrated under reduced pressure. The residue was dried under vacuum for 1 h and dissolved in CH$_2$Cl$_2$. An excess amount of pyrrolidine (122 mg, 1.72 mmol) was added to the reaction mixture. Stirred for 1 h, the reaction mixture was treated with water. The organic layer was separated and washed with brine, dried and concentrated. The residue was purified by chromatography on silica gel eluting with CH$_2$Cl$_2$:MeOH (95:5) to give the desired product (150 mg) in 67% yield as a white solid. M+H$^+$(521).

EXAMPLE 17

Preparation of 2-{5-[4-(4-Fluoro-benzyl)-2R,5S-dimethyl-piperazine-1-carbonyl]-6-methoxy-1H-pyrrolo[2,3-b]pyridin-3-yl}-2-oxo-acetamide

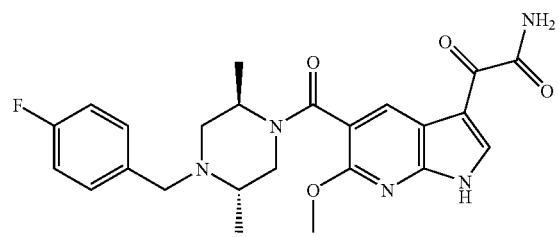

Prepared according to the procedure in Example 16, Step H using ammonia in place of pyrrolidine. M+H$^+$(468).

EXAMPLE 18

Preparation of 2-{5-[4-(4-Fluoro-benzyl)-2R,5S-dimethyl-piperazine-1-carbonyl]-6-methoxy-1H-pyrrolo[2,3-b]pyridin-3-yl}-N-methyl-2-oxo-acetamide

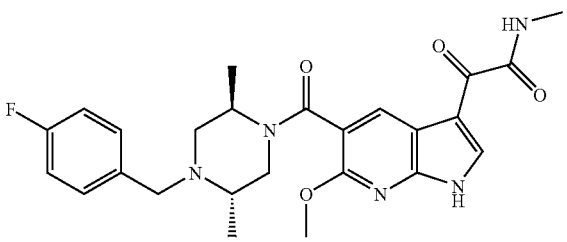

Prepared according to the procedure in Example 16, Step H using methylamine in place of pyrrolidine. M+H$^+$(482)

EXAMPLE 19

Preparation of 2-{5-[4-(4-Fluoro-benzyl)-2R,5S-dimethyl-piperazine-1-carbonyl]-6-ethoxy-1H-pyrrolo[2,3-b]pyridin-3-yl}-N-methyl-2-oxo-acetamide

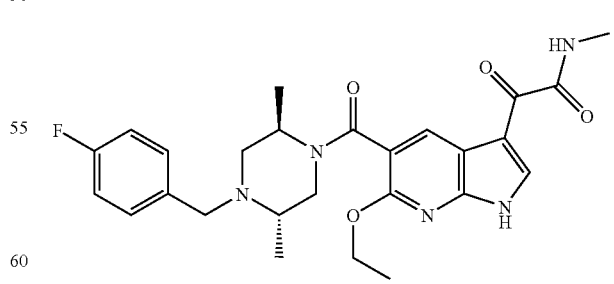

Prepared similarly to Example 26 (below) however, using sodium ethoxide instead of sodium methoxide in step E and coupling with 4-fluorobenzyl-2S,5R-dimethyl piperazine in place of 1-[1-(4-fluoro-phenyl)-ethyl]-3-methyl-piperazine in Step M. M+H$^+$(496)

EXAMPLE 20

Preparation of 2-{5-[4-(4-Fluoro-benzyl)-2R,5S-dimethyl-piperazine-1-carbonyl]-6-methoxy-1H-pyrrolo[2,3-b]pydridin-3-yl}-N,N-dimethyl-2-oxo-acetamide

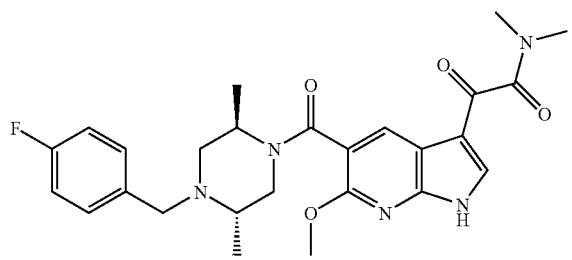

Prepared according to the procedure in Example 16, Step H using dimethylamine in place of pyrrolidine. M+H⁺(496).

EXAMPLE 21

Preparation of N-Ethyl-2-{5-[4-(4-fluoro-benzyl)-2R,5S-dimethyl-piperazine-1-carbonyl]-6-methoxy-1H-pyrrolo[2,3-b]pyridin-3-yl}-N-methyl-2-oxo-acetamide

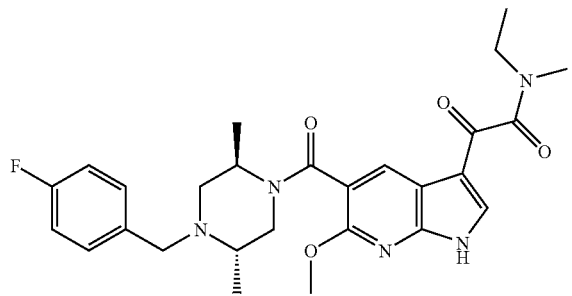

Prepared according to the procedure in Example 16, Step H using methylethylamine in place of pyrrolidine. M+H⁺(510).

EXAMPLE 22

Preparation of 1-{5-[4-(4-Fluoro-benzyl)-2R,5S-dimethyl-piperazine-1-carbonyl]-6-methoxy-1H-pyrrolo[2,3-b]pyridin-3-yl}-2-(3-hydroxy-pyrrolidin-1-yl)-ethane-1,2-dione

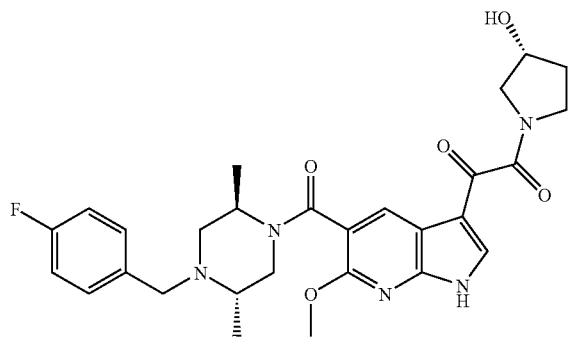

Prepared according to the procedure in Example 16, Step H using 3-hydroxypyrrolidine in place of pyrrolidine. M+H⁺ (538).

EXAMPLE 23

Additional Compounds

The synthesis of the following compounds can be carried out in a manner similar to the procedure described in Example 10.

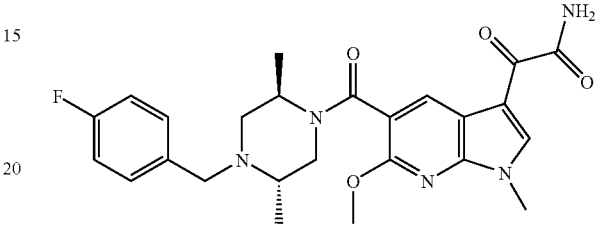

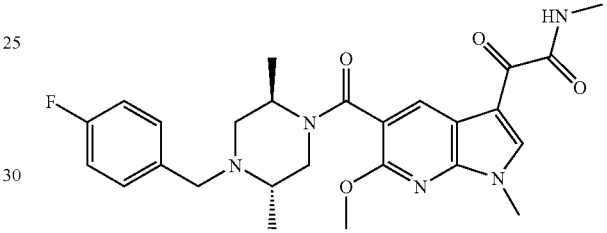

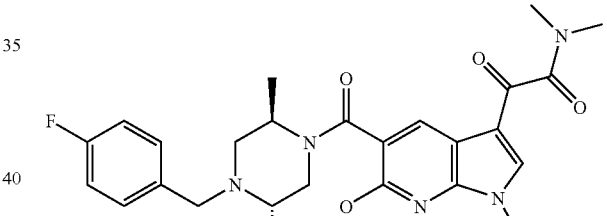

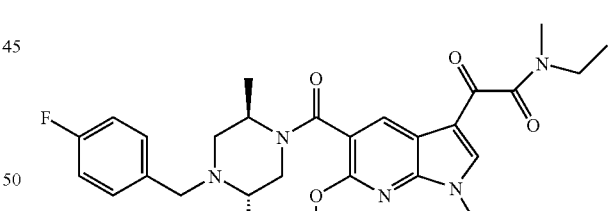

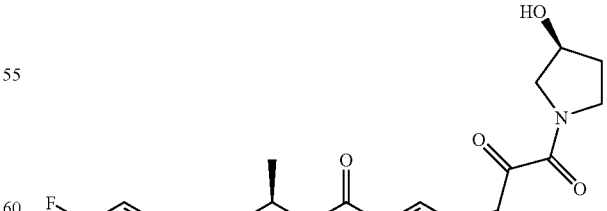

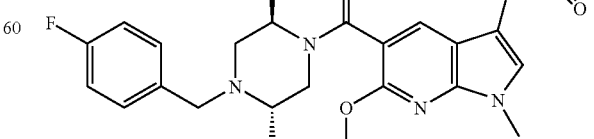

-continued
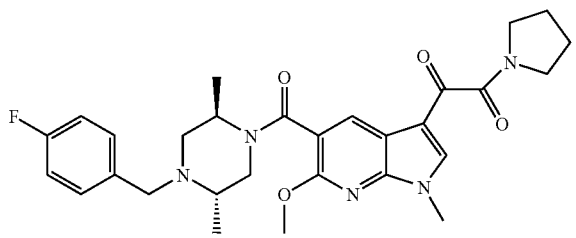
EXAMPLE 24
Additional Compounds
The synthesis of the following compounds can be carried out in a manner similar to the procedure described in Example 12.
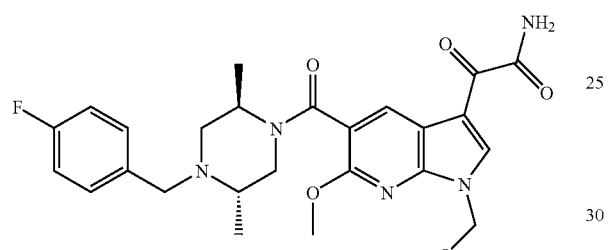
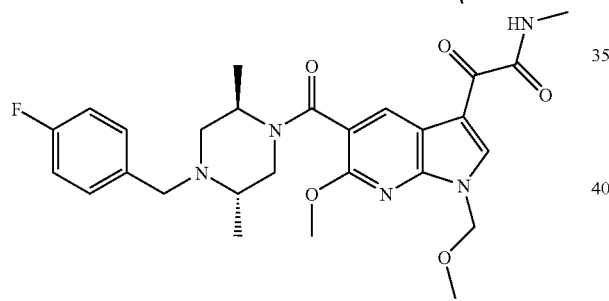
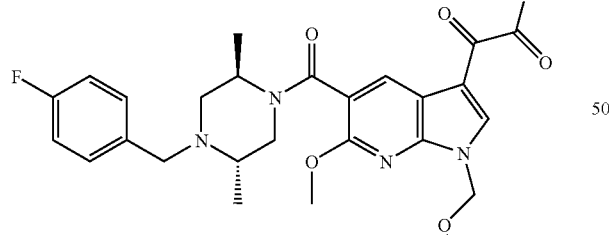
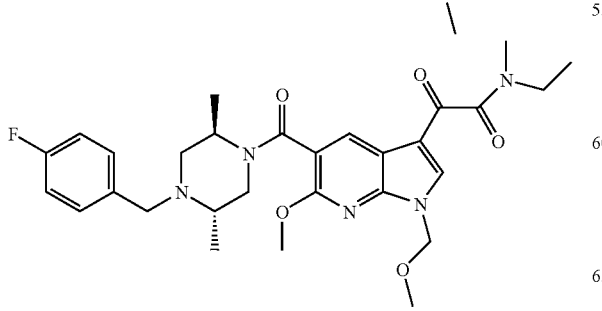
-continued
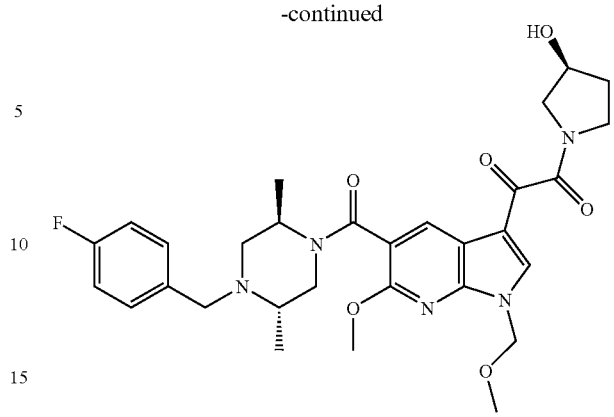
EXAMPLE 25
Additional Compounds
The synthesis of the following compounds can be carried out in a manner similar to the procedure described in Example 14.
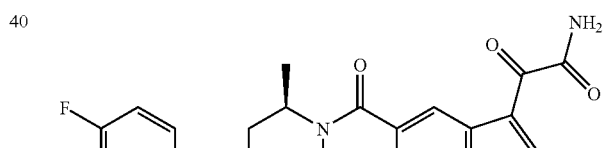
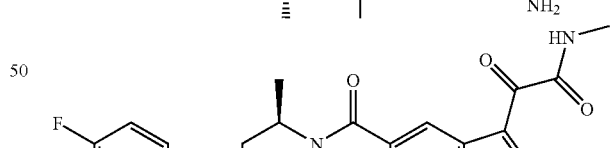
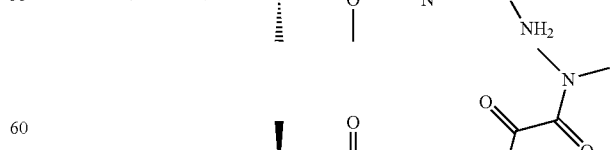
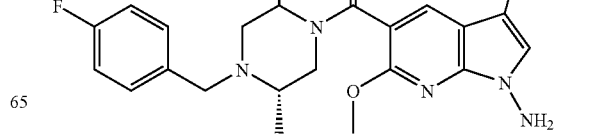

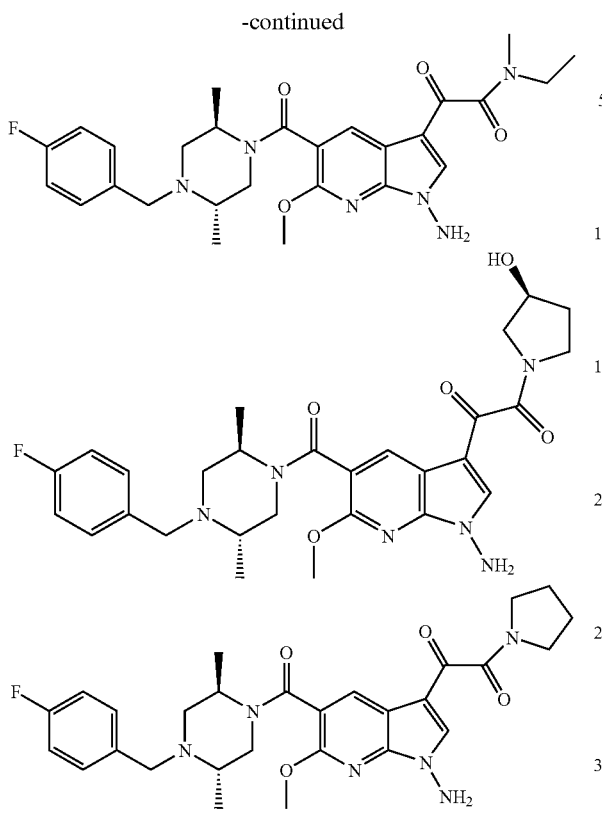

Examples 26-30 are provided using an alternative method to synthetic scheme 1, as described in schemes 3-5.

EXAMPLE 26

Preparation of 2-(5-{4-[1-(4-Fluoro-phenyl)-ethyl]-2R-methyl-piperazine-1-carbonyl}-6-methoxy-1H-pyrrolo[2,3-b]pyridin-3-yl)-N-methyl-2-oxo-acetamide

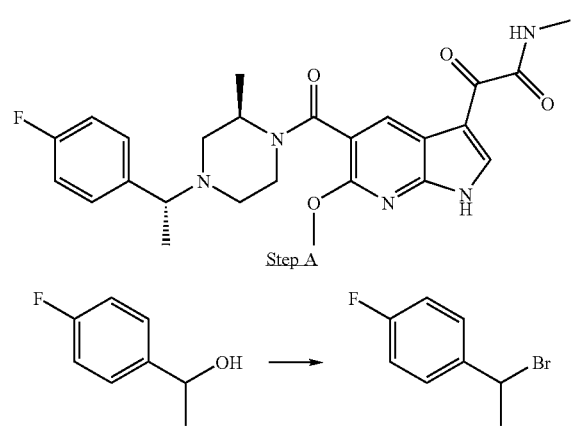

4-Fluoro-α-methylbenzyl alcohol (7 g, 6.3 ml, 50 mmol) was added to 50 mL 48% aqueous solution of HBr at 0° C. The solution was allowed to stir 3 h at RT, at which time it was extracted with hexane. After drying and concentration, 10 g of a colorless oil was obtained. M+H⁺(203).

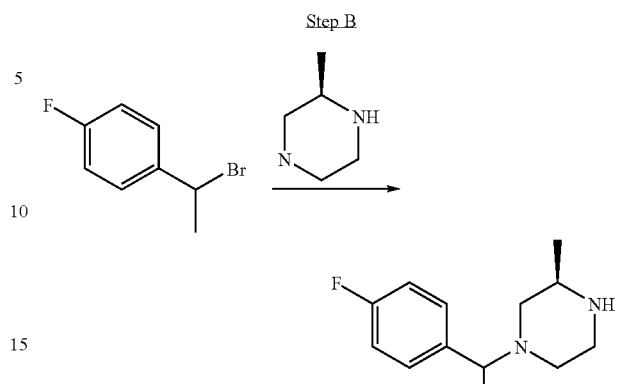

To 6.4 g 1-(4-fluorophenyl)-ethyl bromine in 100 mL DMF was added the piperazine. The mixture was then stirred overnight at room temperature. The solution was evaporated and the residue was then filtrated on a small quantity of silica gel, washing with ethyl acetate and methanol. Purification was carried out using flash chromatography, CHCl₃/MeOH/Et₃N=90/8/2 (or AcOEt/MeOH=90/10). 6.2 g (90%) of pure compound (mixture inseparable of two diasteromers) was obtained. M+H⁺(223).

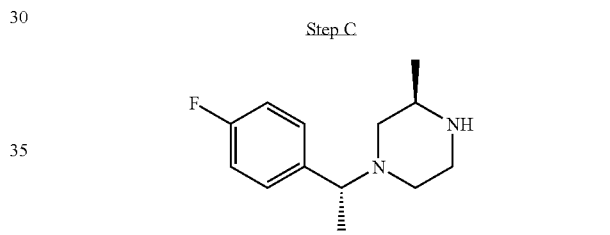

Separation of Diastereomers

To the mixture of two diastereomers (1 g, 4.5 mmol) in methanol (2.5 mL), was added a solution of L-tartaric acid (1.4 g, 9 mmol) in methanol (4.2 mL). Crystallization is effected by keeping the resulting mixture at 0° C. over 30 h. The resulting material was filtered and then 15% NaOH was added to the mother liquid. The free base was extracted with ethyl acetate. Upon concentrated the resulting colorless oil was recrystallized in hexane two or three times until the desired purity is obtained (determined by proton NMR). M+H⁺(223).

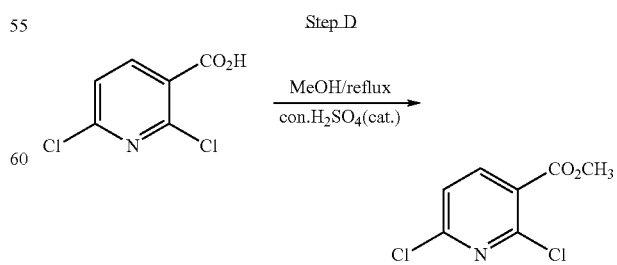

To a solution of 2,6-dichloronicotinic acid (30 g, 0.16 mol) in 150 mL methanol was added 3 mL of con. H₂SO₄ and the mixture was refluxed for 12 h. The methanol was evaporated off and the residue was dissolved in ethyl acetate, washed with water, 10% sodium carbonate solution, brine, dried with sodium sulfate and evaporated to yield the desired product (29.0 g, 87%) as white solid.

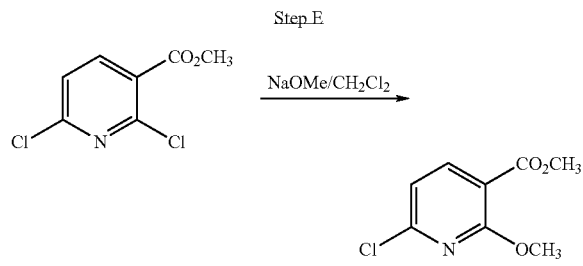

To a solution of 2,6-Dichloro-nicotinic acid methyl ester (20.0 g, 0.1 mol) in dichlomethane (80 ml) at 0° C. was added NaOMe (8.1 g, 0.15 mol) slowly and stirred at 0° C. for 3 h. The reaction mixture was diluted with water, the organic layer was dried with sodium sulfate and evaporated to give an oily product which slowly solidified into a white solid (14.0 g, 70%).

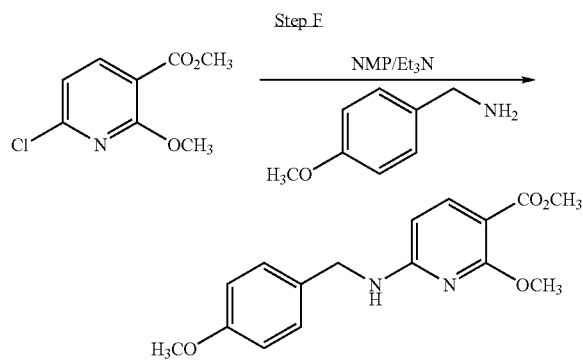

To a solution of 6-Chloro-2-methoxy-nicotinic acid methyl ester (18.5.0 g, 0.092 mol) in 50 mL of NMP was added p-methoxybenzylamine (19.0 g, 0.14 mol) and triethylamine (10.0 g, 0.1 mol). The mixture was heated to 70° C. for 4 h, cooled and diluted with water and extracted with ethyl acetate, washed with water, brine, dried with sodium sulfate, and evaporated to get an oil which was precipitated with ethylacetate/hexane mixture (1:1). This was then filtered and dried to yield 15 g (60%) of the target compound.

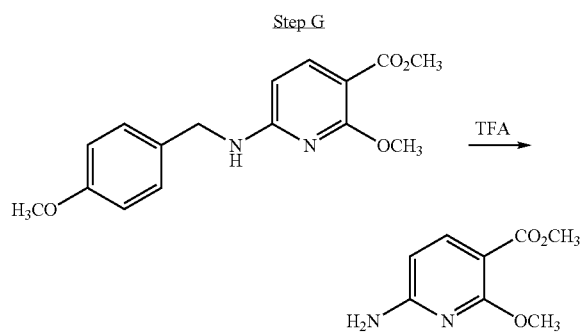

To the 2-methoxy-6-(4-methoxy-benzylamino)-nicotinic acid methyl ester was added TFA (50 mL) and the mix was warmed to 40° C. for 4 h. Most of the TFA was evaporated off and the residue was suspended in ethyl acetate/20% potassium carbonate and filtered through a celite pad. The organic layer was separated, dried with sodium sulfate and evaporated to get 5.4 g (65%) of the product as white solid.

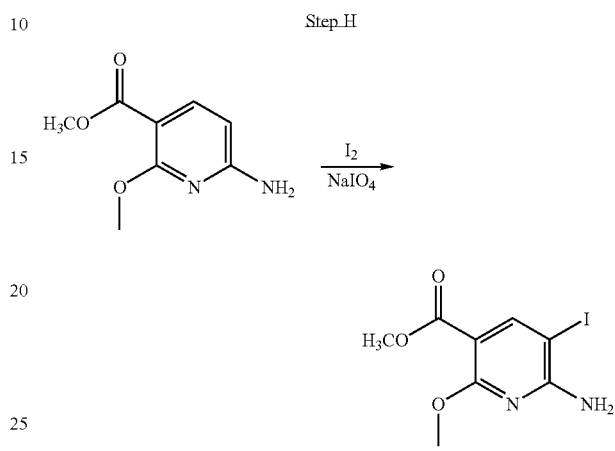

6-Amino-2-methoxy-nicotinic acid methyl ester (20 g, 109.89 mmol) was taken in DMF (100 mL) and iodine (22.4 g, 88 mmol) and $NaIO_4$ (9.42 g, 44 mmol) were added. The mixture was stirred at 50° C. for 5 h under a nitrogen atmosphere. It was then poured into water and the product was extracted with ethyl acetate. The extract was decolorized using aqueous sodium thiosulphate solution. It was further washed with water, dried over sodium sulfate and concentrated. The crystallized product was collected by filtration. Further concentration of the mother liquor provided another crop to yield 22.25 g of the desired product. LCMS: 309.

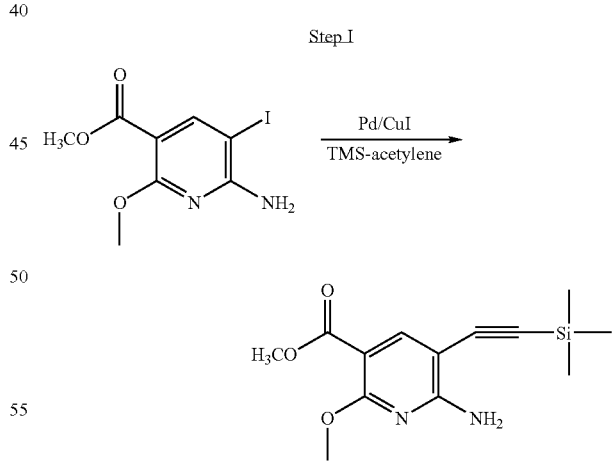

6-Amino-5-iodo-2-methoxy-nicotinic acid methyl ester (19.04 g, 61.82 mmol) was taken in dichloromethane (190 mL) and triethylamine (13 mL, 93 mmol) and $Pd(PPh)_2Cl_2$ (220 mg, 0.31 mmol) and CuI (411 mg, 2.16 mmol) were added. The mixture was cooled in an ice-bath and trimethylsilylacetylene (9.61 mL, 68 mmol) was added dropwise. The mixture was stirred over ice for another 30 min after which the ice-bath was removed and stirring continued for another 5 h. It was filtered to remove the solids and evaporated to dryness. The product was purified on a column of silica eluting it with ethyl acetate-hexane (0 to 20% ethyl acetate, gradient) to yield 15.69 g of the desired product. LCMS: 279.

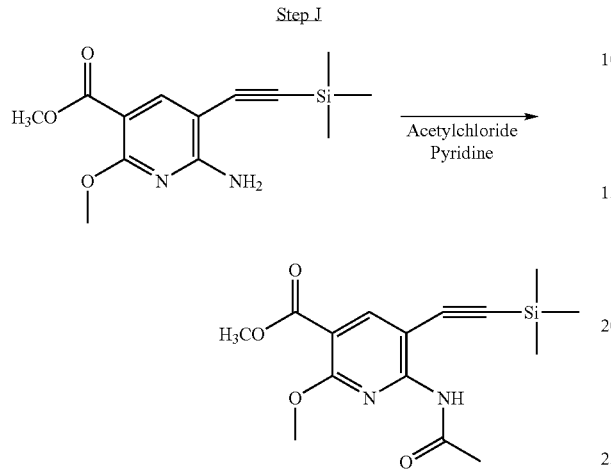

16-Amino-2-methoxy-5-trimethylsilanylethynylnicotinic acid methyl ester (24.63 g, 88.6 mmol) was taken in dichloromethane (250 mL) and pyridine (14.3 mL, 177.2 mmol) was added. The mixture was cooled in an ice-bath and acetyl chloride (7.56 mL, 106.32 mmol) was added dropwise. After 1 h the ice-bath was removed and stirring continued under nitrogen for 20 h. The reaction mixture was washed with water, dried and evaporated. The residue was purified in a column of silica gel eluting with ethyl acetate-hexane (0 to 30% ethyl acetate, gradient) to yield 23.42 g of the desired product. LCMS: 321.

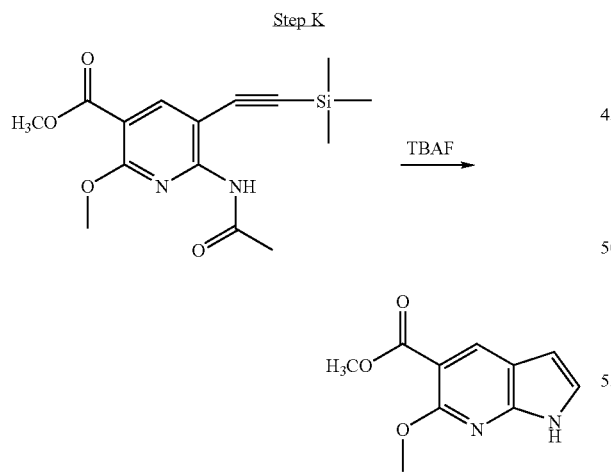

6-Acetylamino-2-methoxy-5-trimethylsilanylethynyl-nicotinic acid methyl ester (18 g, 56.25 mmol) of was dissolved in dry THF (50 mL) and TBAF (1M solution in THF, 225 mL, 225 mmol) was added and the mixture refluxed for 20 h. The volatiles were removed and the residue was extracted with dichloromethane from water. The extract was dried over sodium sulfate, concentrated and purified on a column of silica gel, eluting it with ethyl acetate-hexane (0 to 25% ethyl acetate, gradient) to yield 10.0 g of the desired product. LCMS: 207.

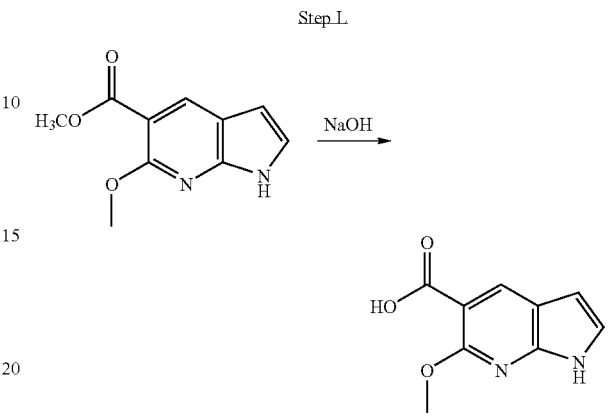

6-Methoxy-1H-pyrrolo[2,3-b]pyridine-5-carboxylic acid methyl ester (2.06 g, 10 mmol) was taken in methanol (50 mL) and 10% aqueous NaOH (16 mL), and water (10 mL) were added. The mixture was then refluxed for 2 h. It was evaporated to remove the methanol, diluted with water and acidified with 10% HCl. The precipitated product was extracted with ethyl acetate, dried over sodium sulfate and evaporated to yield 1.93 g of the desired product. LCMS: 193.

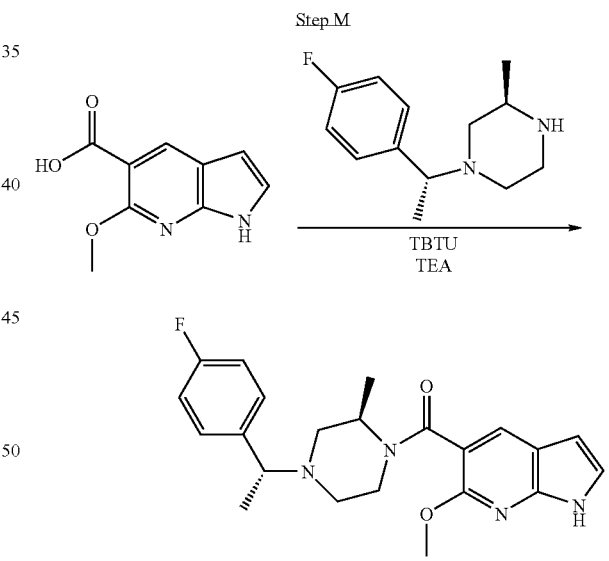

6-Methoxy-1H-pyrrolo[2,3-b]pyridine-5-carboxylic acid (395 mg, 2 mmol) and 1-[1-(4-fluoro-phenyl)-ethyl]-3-methyl-piperazine (888 mg, 4 mmol) were dissolved in dry DMF (15 mL) and TBTU (1.28 g, 4 mmol) was added followed by TEA (600 mg, 6 mmol). The mixture was stirred for 20 h. It was poured into water and the product was extracted out with ethyl acetate. The extract was dried, evaporated and purified on a column of silica gel eluting it with ethyl acetate-hexane (20-40% ethyl acetate, Gradient) to yield 510 mg of the desired product. LCMS: 397.

Step N

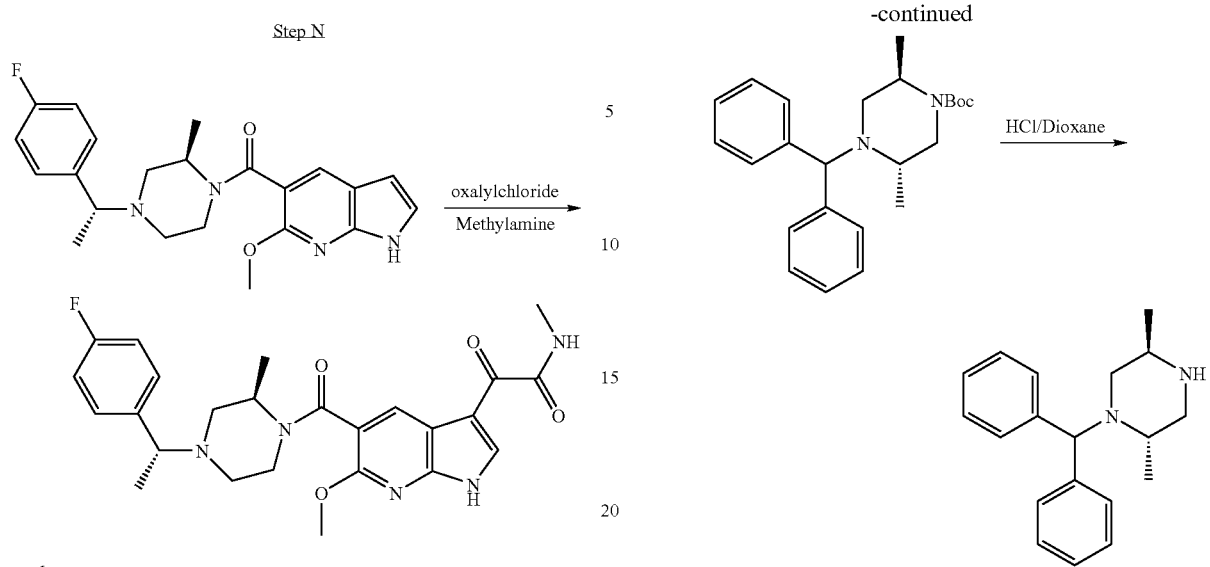

{4-[1-(4-Fluoro-phenyl)-ethyl]-2-methyl-piperazin-1-yl}-(6-methoxy-1H-pyrrolo[2,3-b]pyridin-5-yl)-methanone (510 mg, 1.28 mmol) was taken in dry dichloromethane (10 mL) and was cooled in an ice-bath. Oxalylchloride (2 M solution in dichloromethane, 5 mL) was added and the mixture stirred under nitrogen for 1 h. The ice-bath was removed and stirring continued for another 6 h at RT. It was evaporated to dryness and resuspended in dry dichlormethane (15 mL) and was cooled in an ice bath. Methylamine (2 M solution in THF, 5 mL) was added via a syringe and stirring was continued for 30 min. This was poured into water and the product was extracted with dichloromethane. The extract was dried, evaporated and the residue was purified by radial chromatography using CHCl$_3$-methanol (0 to 3% methanol) as eluant to yield 310 mg of the desired product. LCMS: 482.

EXAMPLE 27

Preparation of 2-[5-(4-Benzhydryl-2R,5 S-dimethyl-piperazine-1-carbonyl)-6-methoxy-1H-pyrrolo[2,3-b]pyridin-3-yl]-N,N-dimethyl-2-oxo-acetamide The crude material was dissolved in acetonitrile (600 mL) and potassium iodide (45.2 g, 272 mmol), potassium carbonate (37.7 g, 272 mmol) and α-bromodiphenylmethane (73.9 g, 299 mmol) were added. The mixture was stirred at room temperature overnight and the solvent was removed. The residue was taken up in EtOAc, washed with 5% potassium carbonate, brine, dried over sodium sulfate and concentrated. This material was dissolved in 4 M HCl in dioxane and stirred for 1 h. After removal of the solvent, the residue was dissolved in EtOAc, washed with 10% NaOH, brine, dried over sodium sulfate and concentrated to give crude 1-benzhydryl-2S,5R-dimethyl-piperazine which was purified using flash chromatography (EtOAc/hexanes) to give 37 g pure 1-benzhydryl-2S,5R-dimethyl-piperazine. M+H$^+$(281).

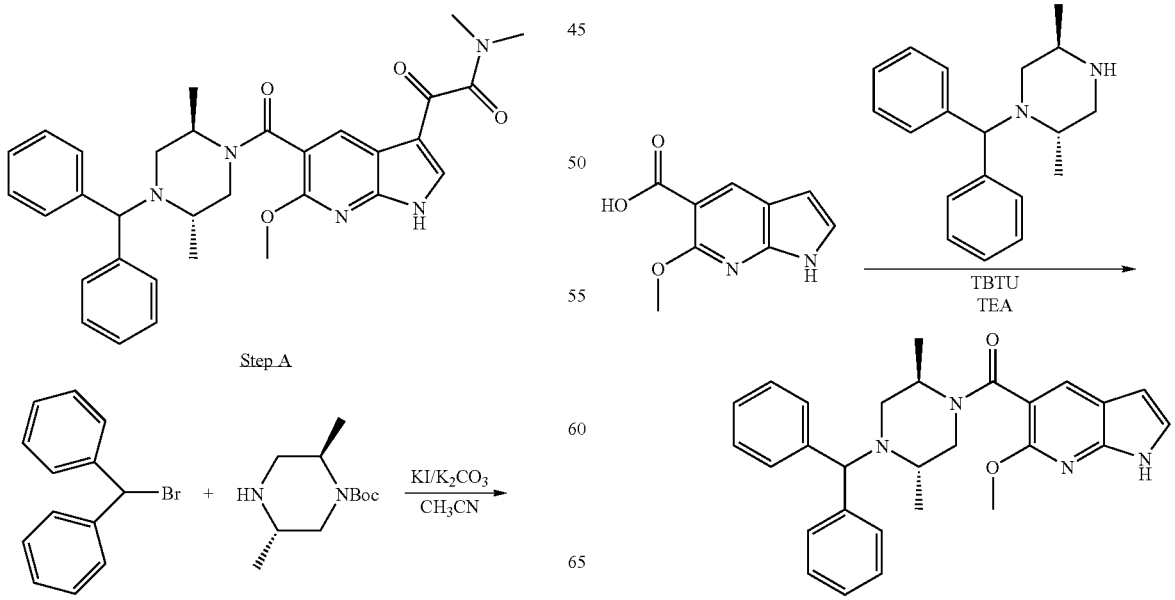

Prepared from 6-Methoxy-1H-pyrrolo[2,3-b]pyridine-5-carboxylic acid and 1-Benzhydryl-2S,5R-dimethyl-piperazine according to the procedure described in Example 26, Step M. M+H⁺(455).

EXAMPLE 29

Preparation of 1-[5-(4-Benzhydryl-2R,5 S-dimethyl-piperazine-1-carbonyl)-6-methoxy-1H-pyrrolo[2,3-b]pyridin-3-yl]-2-pyrrolidin-1-yl-ethane-1,2-dione

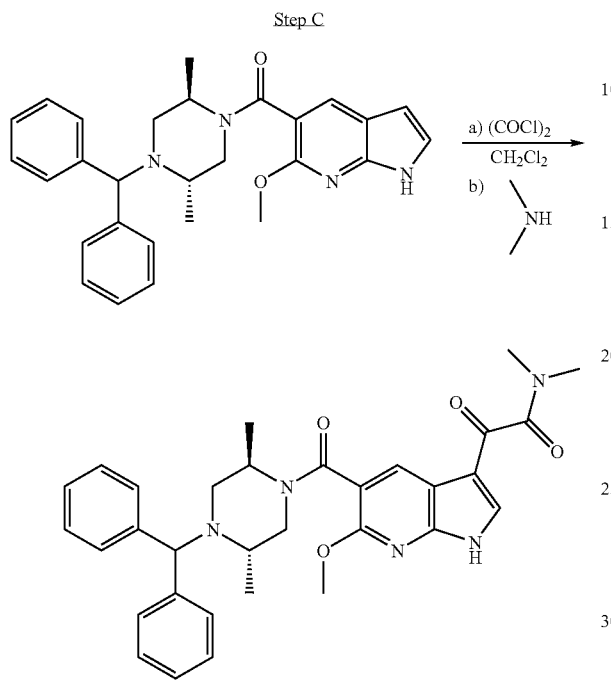

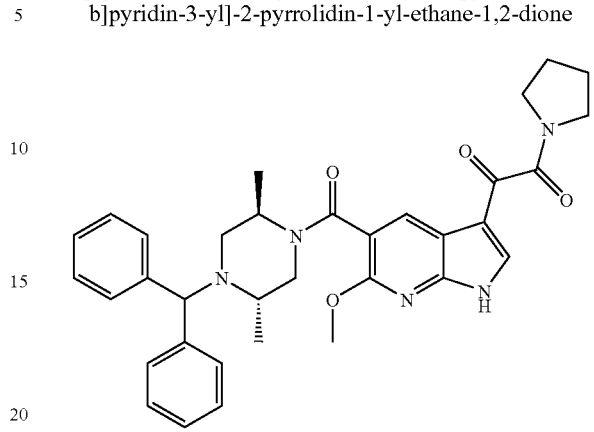

Prepared according to the procedure in Example 27, Step C using pyrrolidine in place of dimethylamine. M+H⁺(580).

EXAMPLE 30

Preparation of 2-[5-(4-Benzhydryl-2R,5S-dimethyl-piperazine-1-carbonyl)-6-methoxy-1H-pyrrolo[2,3-b]pyridin-3-yl]-N-cyclopentyl-2-oxo-acetamide

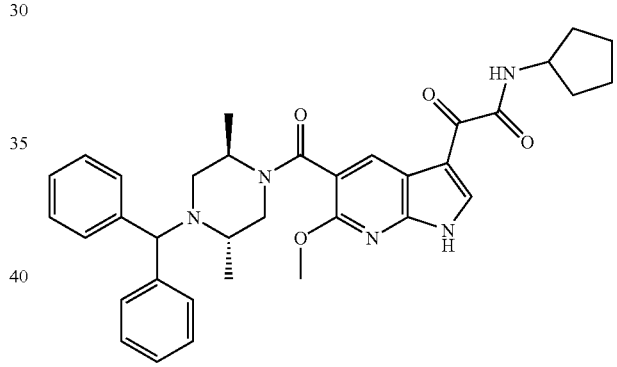

Prepared according to the procedure in Example 16, Step H using dimethylamine in place of pyrrolidine. M+H⁺(554).

EXAMPLE 28

Preparation of 2-[5-(4-Benzhydryl-2R,5S-dimethyl-piperazine-1-carbonyl)-6-methoxy-1H-pyrrolo[2,3-b]pyridin-3-yl]-N-methyl-2-oxo-acetamide Prepared according to the procedure in Example 27, Step C using cyclopentylamine in place of pyrrolidine. M+H⁺(594).

EXAMPLE 31

Preparation of 2-{5-[4-(4-Fluoro-benzyl)-2R-methyl-piperazine-1-carbonyl]-6-methoxy-1H-pyrrolo[2,3-b]pyridin-3-yl}-N-methyl-2-oxo-acetamide

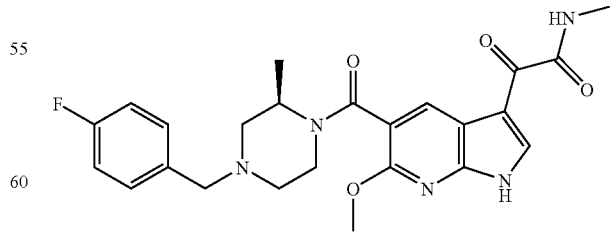

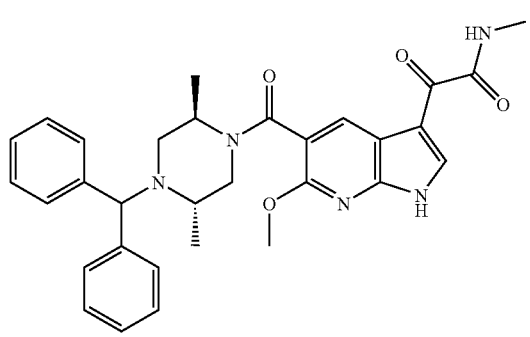

Prepared according to the procedure in Example 27, Step C using methylamine in place of dimethylamine. M+H⁺(540).

Prepared similarly to Example 26 however, coupling with 4-fluorobenzyl-3R-methyl piperazine in place of 1-[1-(4-fluoro-phenyl)-ethyl]-3-methyl-piperazine in Step M. M+H⁺ (468)

EXAMPLE 32

Preparation of 2-{5-[4-(4-Fluoro-benzyl)-2R-methyl-piperazine-1-carbonyl]-6-methoxy-1H-pyrrolo[2,3-b]pydridin-3-yl}-2-oxo-acetamide

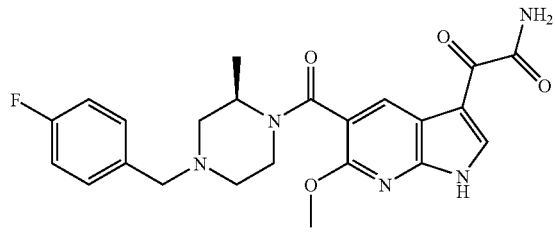

Prepared similarly to Example 26 however, coupling with 4-fluorobenzyl-3R-methyl piperazine in place of 1-[1-(4-fluoro-phenyl)-ethyl]-3-methyl-piperazine in Step M and using ammonia in place of methylamine in Step N. M+H+ (454).

EXAMPLE 33

Preparation of 2-{6-Ethoxy-5-[4-(4-fluoro-benzyl)-2R,5S-dimethyl-piperazine-1-carbonyl]-1H-pyrrolo[2,3-b]pyridin-3-yl}-2-oxo-acetamide

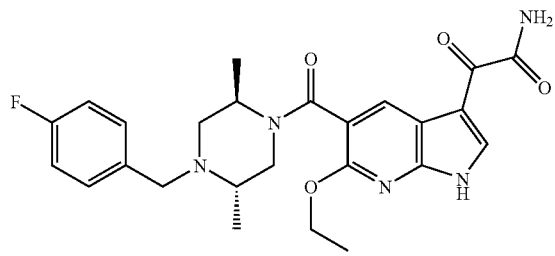

Prepared similarly to Example 26 however, using sodium ethoxide instead of sodium methoxide in step E, coupling with 4-fluorobenzyl-2S,5R-dimethyl piperazine in place of 1-[1-(4-fluoro-phenyl)-ethyl]-3-methyl-piperazine in Step M, and using ammonia in place of methylamine in Step N. M+H+(482).

EXAMPLE 34

Preparation of 2-{6-Ethoxy-5-[4-(4-fluoro-benzyl)-piperidine-1-carbonyl]-1H-pyrrolo[2,3-b]pyridin-3-yl}-N-methyl-2-oxo-acetamide

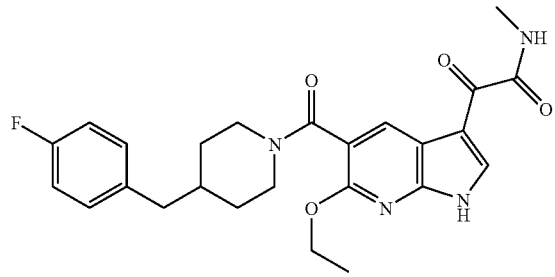

Prepared similarly to Example 26 however, using sodium ethoxide instead of sodium methoxide in step E and coupling with 4-fluorobenzyl-piperidine in place of 1-[1-(4-fluoro-phenyl)-ethyl]-3-methyl-piperazine in Step M. M+H+(467).

EXAMPLE 35

Preparation of 2-{6-Ethoxy-5-[4-(4-fluoro-benzyl)-piperidine-1-carbonyl]-1H-pyrrolo[2,3-b]pyridin-3-yl}-2-oxo-acetamide

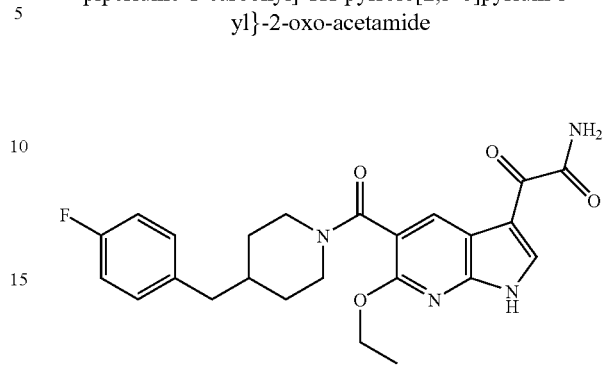

Prepared similarly to Example 26 however, using sodium ethoxide instead of sodium methoxide in step E, coupling with 4-fluorobenzyl-piperidine in place of 1-[1-(4-fluoro-phenyl)-ethyl]-3-methyl-piperazine in Step M, and using ammonia in place of methylamine in Step N. M+H+(453).

EXAMPLE 36

Preparation of 2-{5-[4-(4-Fluoro-benzyl)-2R,5S-dimethyl-piperazine-1-carbonyl]-6-methyl-1H-pnrrolo[2,3-b]pyridin-3-yl}-N,N-dimethyl-2-oxo-acetamide

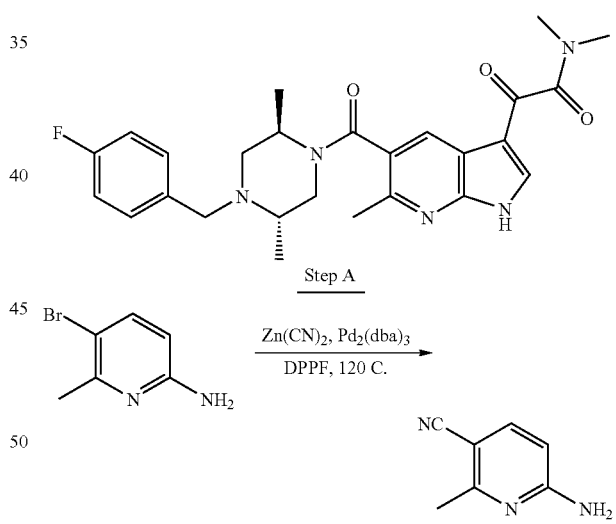

To the degassed DMF solution of aminopyridine (2 g), Zn(CN)$_2$ (753 mg) and 1,1-bis(diphenylphosphoino)ferrocene (DPPF) (711 mg) was added Pd$_2$(dba)$_3$ (489 mg). The reaction was heated to 130° C. in a sealed tube for 3 days. The reaction was then cooled to 85° C. and diluted with 200 ml NH$_4$Cl (Sat'd), H$_2$O and NH$_2$OH (4:4:1). The mixture was then stirred for overnight at 85° C. After cooling to RT, the reaction mixture was filtered and the filtrate was extracted with EtOAc. The combined organic layers was washed with water, brine, and then dried over Na$_2$SO$_4$. After removing solvent, the residue was purified with normal phase silica gel column eluting with 0-50% EtOAc in Hexane.

Step B

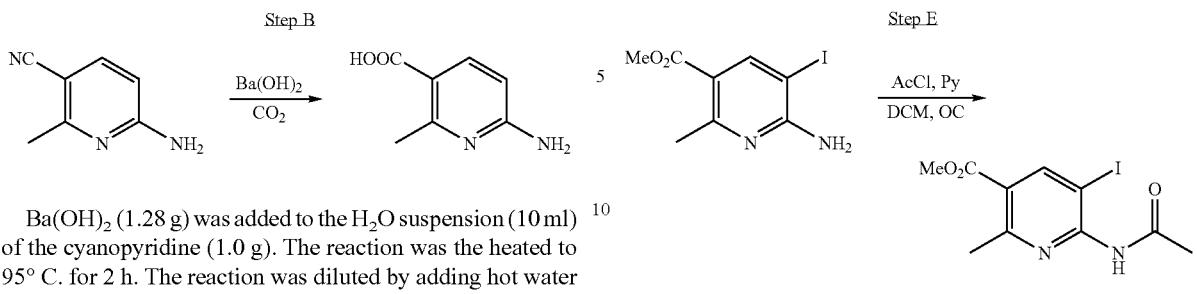

Ba(OH)₂ (1.28 g) was added to the H₂O suspension (10 ml) of the cyanopyridine (1.0 g). The reaction was the heated to 95° C. for 2 h. The reaction was diluted by adding hot water followed by the addition of celite. While the temperature was held at 95° C., CO₂ gas was passed through the reaction mixture for 30 min to saturate the reaction mixture until the pH=8-9. The reaction was filtered and the filter cake was washed with hot water three times. The combined water solution was evaporated under vacuum and gave 1.0 g of a white solid as the crude product.

Step C

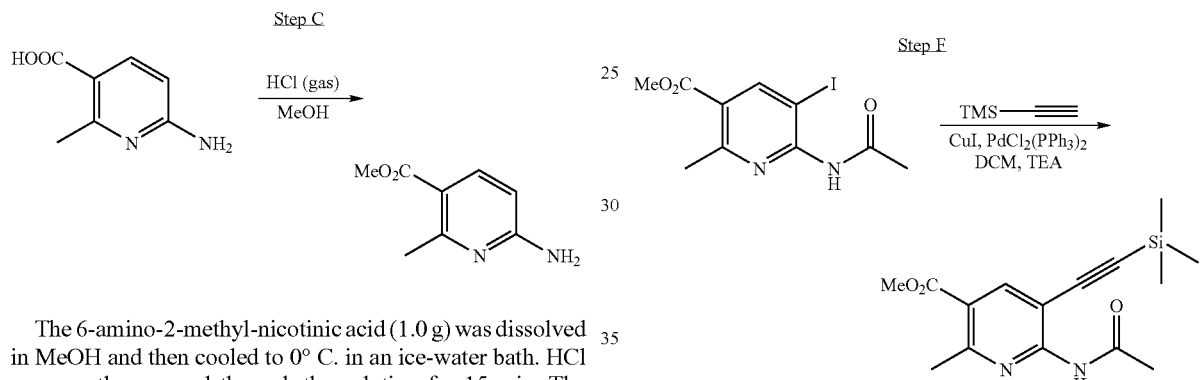

The 6-amino-2-methyl-nicotinic acid (1.0 g) was dissolved in MeOH and then cooled to 0° C. in an ice-water bath. HCl gas was then passed through the solution for 15 min. The reaction was warmed to RT and stirred overnight. After evaporating the MeOH, the residue was neutralized with saturated solution of Na₂CO₃ and extracted with EtOAc. The combined organic layers were washed with water and brine then dried over Na₂SO₄ Removing solvent give 500 mg crude product that was carried on to the next step without further purification.

Step D

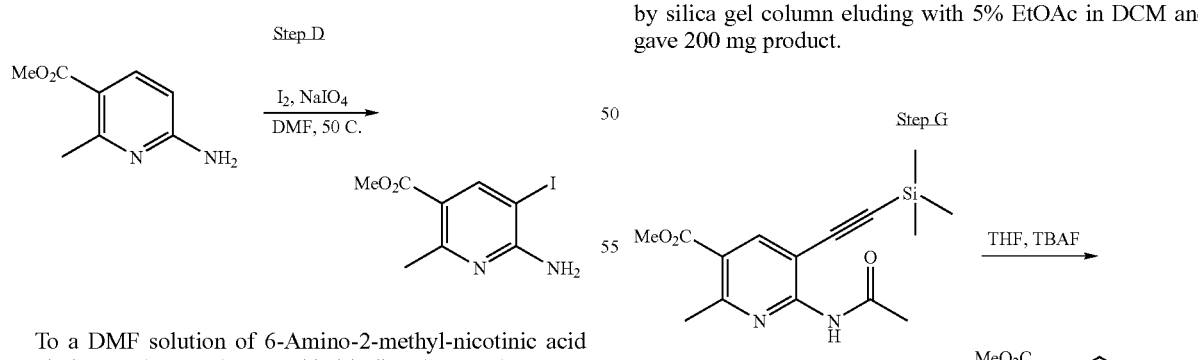

To a DMF solution of 6-Amino-2-methyl-nicotinic acid methyl ester (500 mg) was added iodine (644 mg), NaIO₄ (754 mg) sequentially. The reaction was then heated to 50° C. overnight. After cooling down to RT, NaHS₂O₃ was added to the reaction until the reaction mixture turned a light yellow color. The mixture was diluted with water and then extracted with EtOAc. The organic layers were combined and washed with water, brine, and dried over Na₂SO₄. Removing the solvent gave 900 mg crude product.

Step E

At 0° C., the acetyl chloride (0.22 ml) was added to the DCM solution of 6-amino-5-iodo-2-methyl-nicotinic acid methyl ester (900 mg) followed by the addition of pyridine (0.38 ml). The reaction was stirred at 0° C. for 1 h, diluted with DCM and washed with water, Na₂CO₃ (Sta'd), water twice and brine. The crude product was purified with column eluding with 25% EtOAc in DCM to give 200 mg product.

Step F

To the DCM solution of 6-acetylamino-5-iodo-2-methyl-nicotinic acid methyl ester (200 mg) was added CuI (17 mg), PdCl₂(PPh₃)₂ (63 mg), TMS acetylene (88 mg), and TEA (2.5 mL) sequentially. The reaction was stirred overnight at RT then diluted with DCM. The mixture was filtered through celite and washed with water and brine then dried over Na₂SO₄. The solvent was evaporated the residue was purified by silica gel column eluding with 5% EtOAc in DCM and gave 200 mg product.

Step G

TBAF (1.3 ml, 1.0M/THF) was added to the THF solution of 6-acetylamino-2-methyl-5-trimethylsilanylethynyl-nicotinic acid methyl ester (200 mg). Reaction was heated under reflux for 4 h. After removing the THF, the residue was dissolved in EtOAc and wash with water and brine. The solvent was removed and the residue was purified by silica gel column eluding with 10-30% EtOAc in DCM to give 70 mg pure product.

Step H

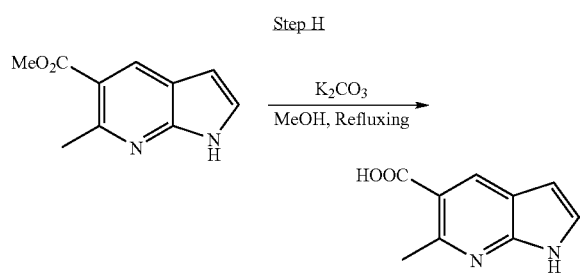

The MeOH suspension of 6-methyl-1H-pyrrolo[2,3-b]pyridine-5-carboxylic acid methyl ester (70 mg) and K$_2$CO$_3$ (76 mg) was heated under refluxing for 4 h. The reaction mixture was then cooled to 0° C. and HCl (6N) was added dropwise until pH 3 was obtained. After removing the MeOH the residue was washed with hot MeOH three times. The combined MeOH solution was evaporated under vacuum to give a yellow solid 120 mg as crude product. The crude product was used directly in the next step.

Step I

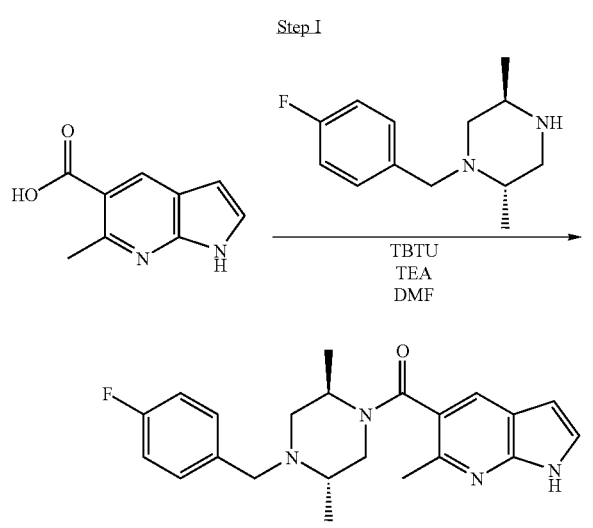

Prepared from 6-methyl-1H-pyrrolo[2,3-b]pyridine-5-carboxylic acid and 1-(4-Fluoro-benzyl)-2S,5R-dimethyl-piperazine according to the procedure described in EXAMPLE 26, Step M.

Step J

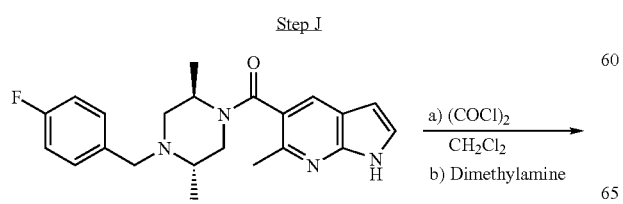

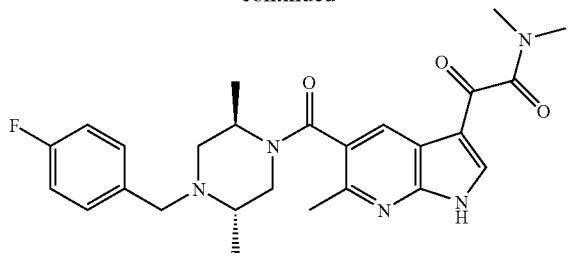

Prepared from [4-(4-fluoro-benzyl)-2R,5S-dimethyl-piperazin-1-yl]-(6-methyl-1H -pyrrolo[2,3-b]pyridin-5-yl)-methanone and dimethylamine according to the procedure described in Example 26, Step N. M+H$^+$(480).

EXAMPLE 37

Additional Compounds

The synthesis of the following compounds can be carried out in a manner similar to the procedure described in Example 36.

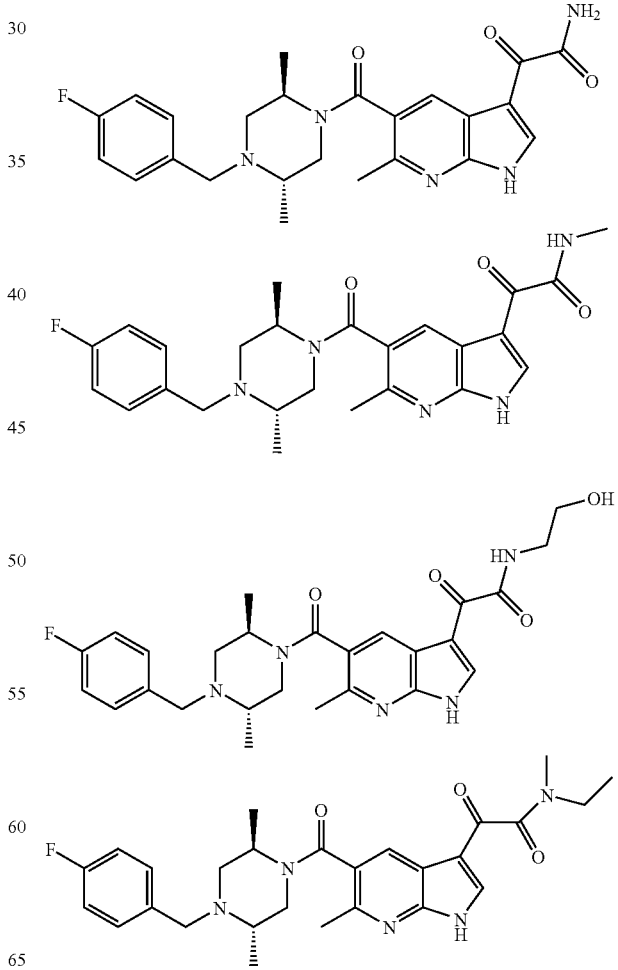

-continued

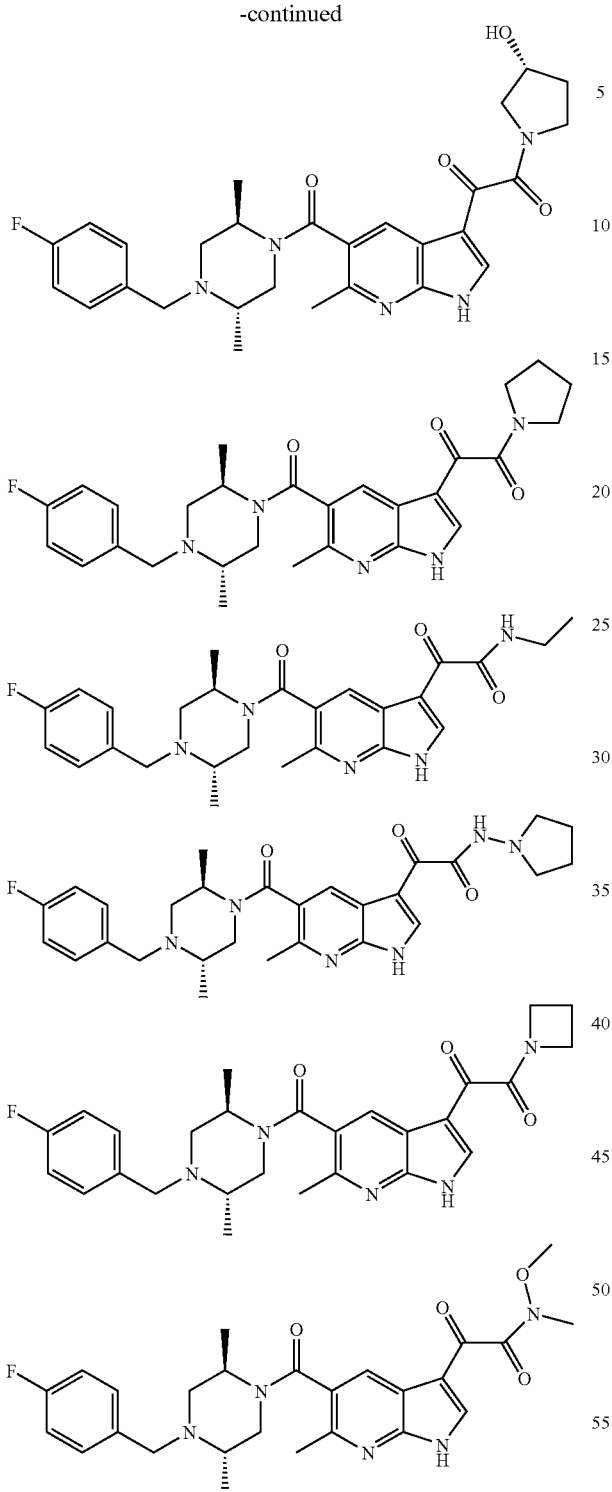

EXAMPLE 38

Biological Activity

The compounds provided herein exhibit varying levels of activity towards p38 kinase. For example, compounds from Examples 1-5, 7-9, 16, 17, 19-22, 26-29, and 31-36 each exhibit an IC$_{50}$ value of 1 µM or less in the diluted Whole Blood Assay described herein.

The invention claimed is:
1. A compound of the formula:

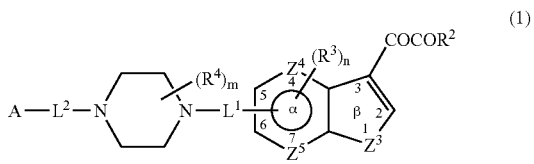

or a pharmaceutically acceptable salt thereof,
wherein R$^2$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, SR, OR, NR$_2$, OCOR, NRCOR, NRCONR$_2$, NRSO$_2$R, NRSO$_2$NR$_2$, OCONR$_2$, CN, COOR, CONR$_2$, COR, or R$_3$Si wherein each R is independently H, alkyl, alkenyl or aryl, or
wherein R$^2$ OR, NR$_2$, SR, NRCONR$_2$, OCONR$_2$, or NRSO$_2$NR$_2$, wherein each R is independently H, alkyl, alkenyl, aryl, heteroalkyl, heteroalkenyl, heteroaryl or heteroarylalkyl, and wherein two R attached to the same atom may form a 3-8 member ring and wherein said ring may further be substituted by alkyl, alkenyl, alkynyl, aryl, arylalkyl, heteroalkyl, heteroalkenyl, heteroaryl, heteroarylalkyl, or optionally substituted with halo, SR, OR, NR$_2$, OCOR, NRCOR, NRCONR$_2$, NRSO$_2$R, NRSO$_2$NR$_2$, OCONR$_2$, or R$_3$Si wherein each R is independently H, alkyl, alkenyl or aryl wherein two R attached to the same atom may form a 3-8 member ring, optionally substituted as above defined;
Z$^3$ is NR$^7$, O, or S;
R$^7$ is hydrogen or is optionally substituted alkyl, optionally substituted acyl, OR, or NR$_2$ wherein each R is independently H, alkyl, alkenyl or aryl;
one of Z$^4$ and Z$^5$ is N and the other of Z$^4$ and Z$^5$ is CH;
each R$^3$ is halo, alkyl, heteroalkyl, OCOR, OR, NRCOR, SR, or NR$_2$, wherein R is H, alkyl, alkenyl, aryl, heteroalkyl, heteroalkenyl, heteroaryl or heteroarylalkyl;
n is 0-3;
L$^1$ CO, SO, SO$_2$, CHOH or CH$_2$;
L$^2$ is alkylene (1-4C) or alkenylene (1-4C) optionally substituted with a moiety selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, NR$_2$ SR, SOR, SO$_2$R, OCOR, NRCOR, NRCONR$_2$, NRCOOR, OCONR$_2$, RCO, COOR, alkyl-OOR, SO$_3$R, CONR$_2$, SO$_2$NR$_2$, NRSO$_2$NR$_2$, CN, CF$_3$, R$_3$Si, and NO$_2$, wherein each R is independently H, alkyl, alkenyl or aryl, and wherein two substituents on L$^2$ can be joined to form a non-aromatic saturated or unsaturated ring that includes 0-3 heteroatoms which are O, S and/or N and which contains 3 to 8 members or said two substituents can be joined to form a carbonyl moiety or an oxime, oximeether, oximeester or ketal of said carbonyl moiety;
each R$^4$ is independently selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, NR$_2$, SR, SOR, SO$_2$R, OCOR, NRCOR, NRCONR$_2$, NRCOOR, OCONR$_2$, RCO, COOR, alkyl-OOR, SO$_3$R, CONR$_2$, SO$_2$NR$_2$, NRSO$_2$NR$_2$, CN, CF$_3$, R$_3$Si, and NO$_2$, wherein each R is independently H, alkyl, alkenyl, aryl, heteroalkyl, heteroalkenyl, heteroaryl or heteroarylalkyl, or $R^4$ is =O or an oxime, oximeether, oximeester or ketal thereof;

m is 0-4; and

A is a cyclic group optionally substituted with 0-5 substituents selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl, heteroaryl or heteroarylalkyl.

2. The compound of claim 1 wherein $R^7$ is H, or is optionally substituted alkyl, optionally substituted acyl, OR, or $NR_2$ wherein each R is independently H, alkyl, alkenyl or aryl.

3. The compound of claim 1 wherein $L^1$ is CO.

4. The compound of claim 1 wherein $L^2$ is unsubstituted alkylene.

5. The compound of claim 4 wherein $L^2$ is unsubstituted methylene.

6. The compound of claim 1 wherein A is optionally substituted phenyl.

7. The compound of claim 6 wherein said optional substitution is by halo, OR, or alkyl.

8. The compound of claim 7 wherein said phenyl is unsubstituted or has a single substituent.

9. The compound of claim 1 wherein each $R^4$ is halo, OR, or alkyl.

10. The compound of claim 9 wherein m is 0, 1, or 2.

11. The compound of claim 10 wherein m is 2 and both $R^4$ are alkyl.

12. The compound of claim 1 wherein $R^3$ is halo or alkoxy.

13. The compound of claim 1 wherein $Z^4$ is N and $Z^5$ CH.

14. The compound of claim 1 wherein $Z^5$ is N and $Z^4$ is CH.

15. A compound selected from the group consisting of

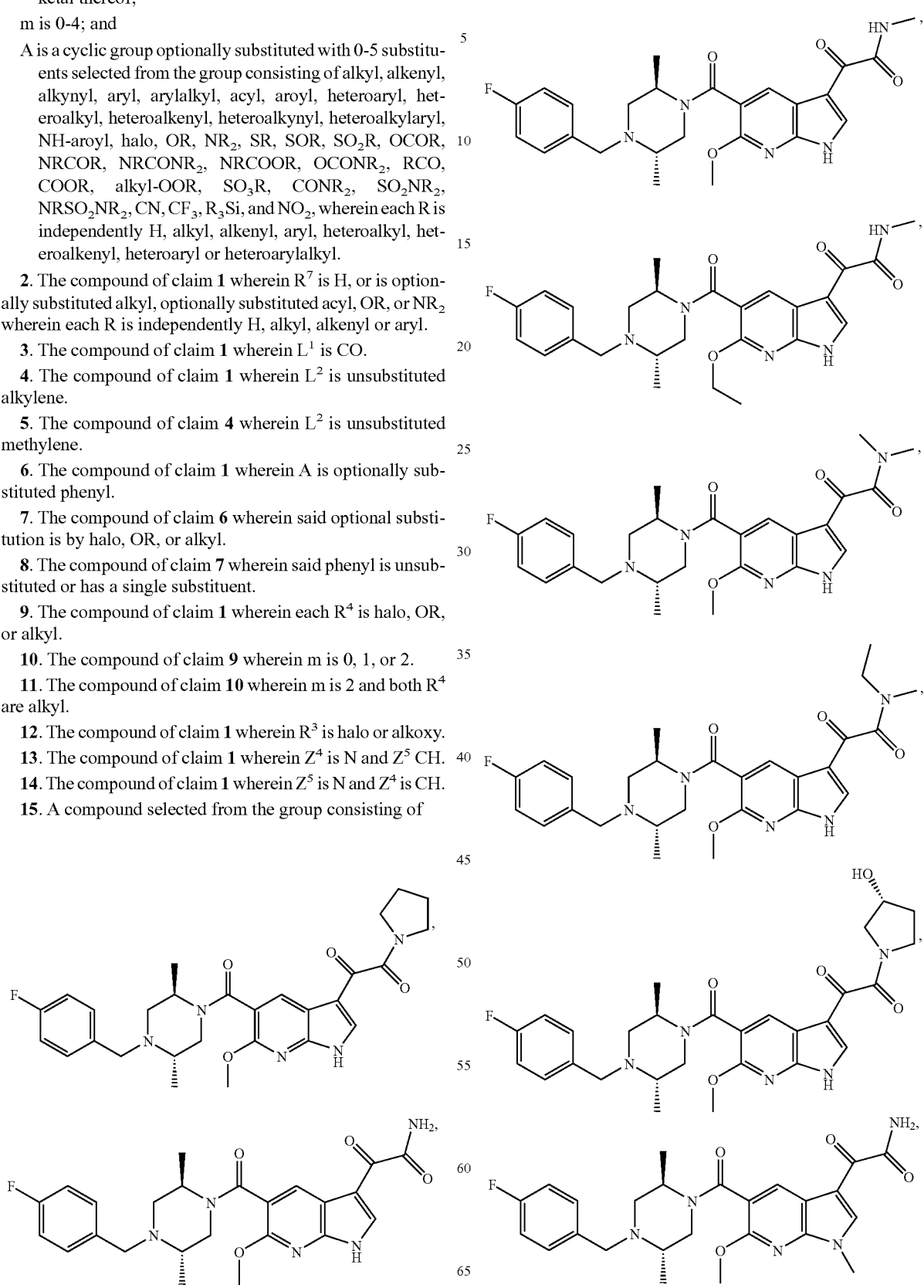

-continued

61
-continued
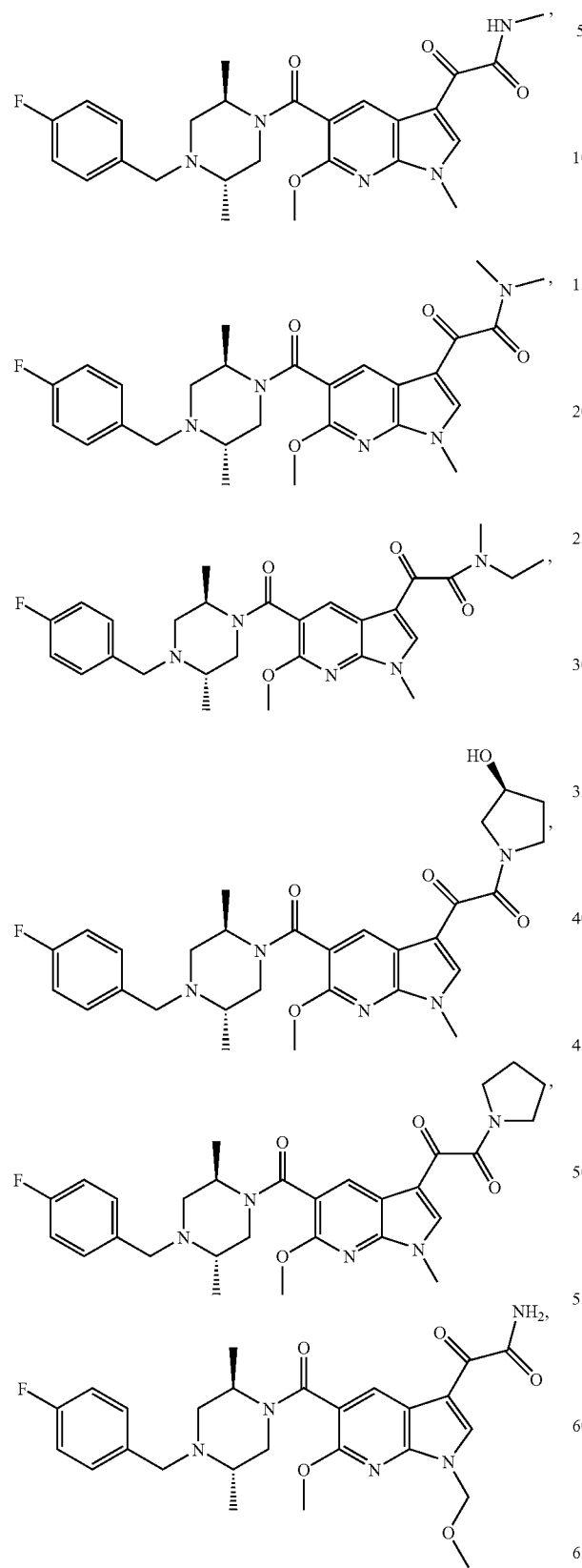
62
-continued
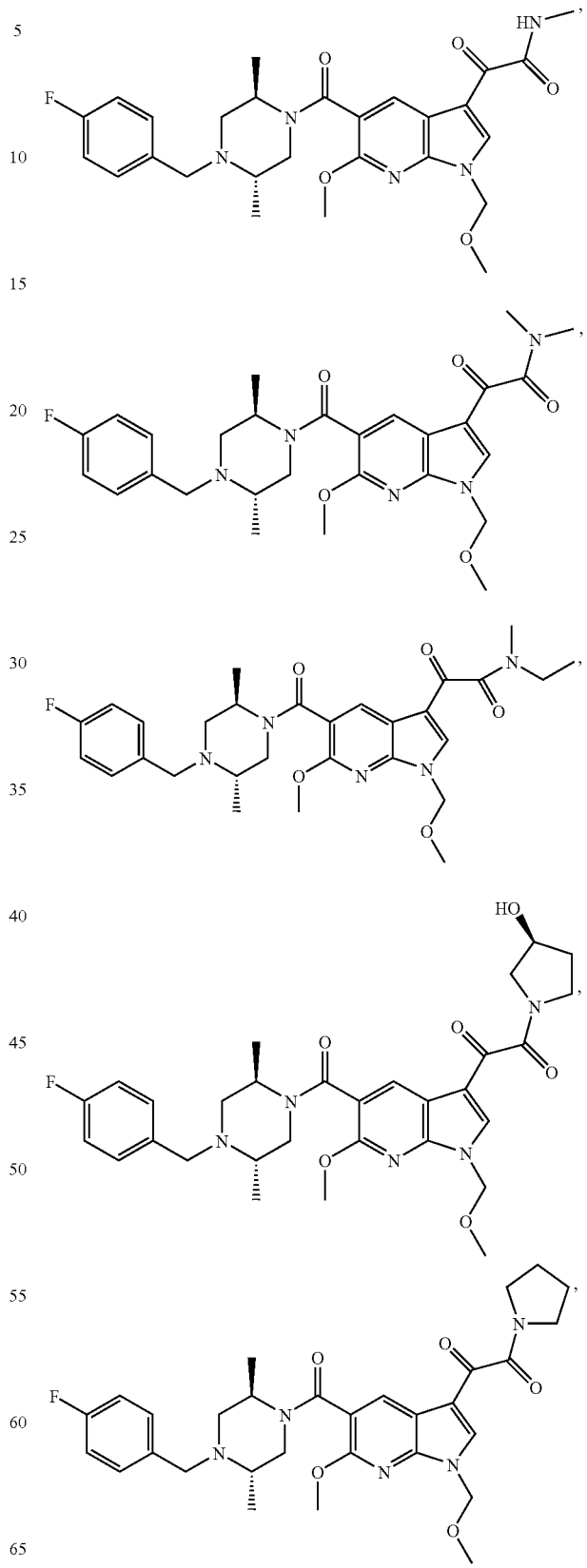

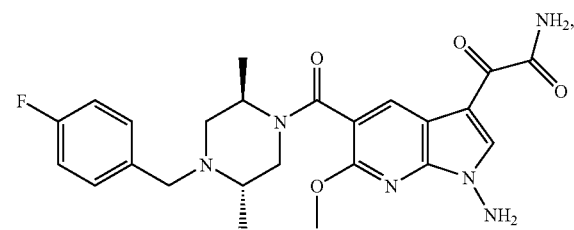
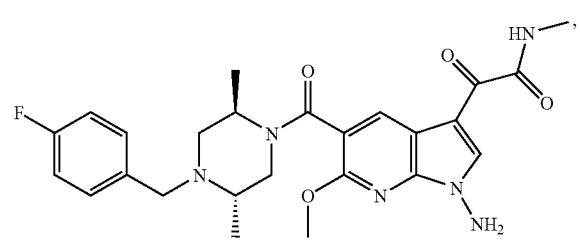
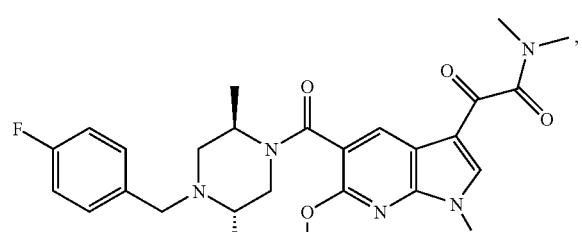
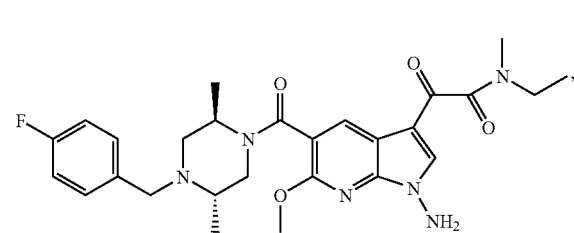
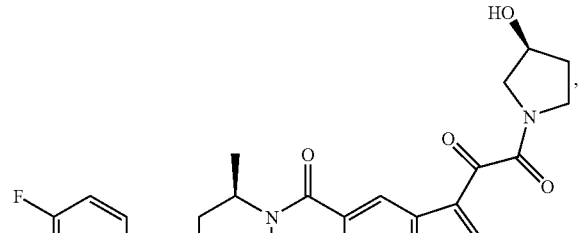
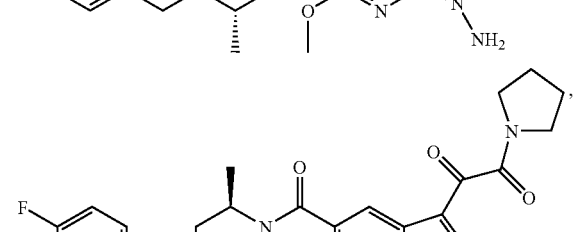
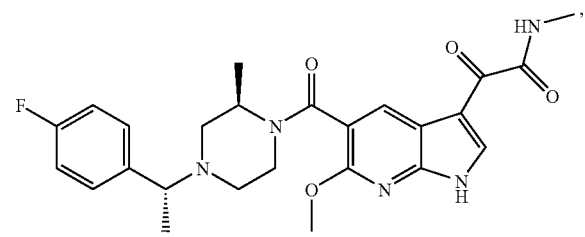
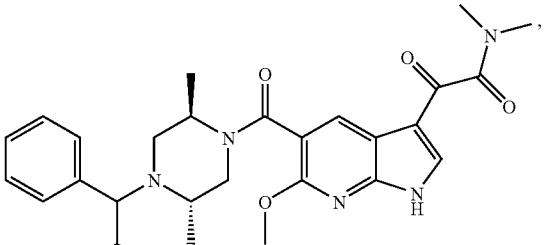
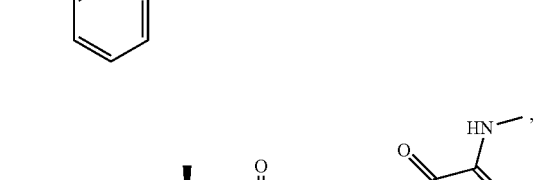
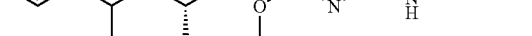
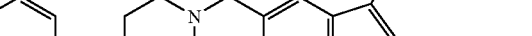

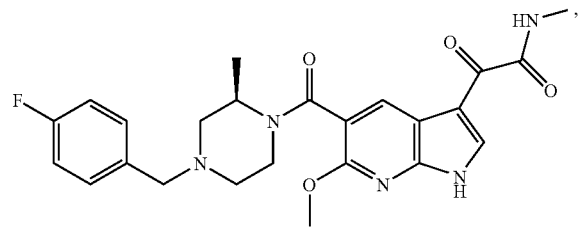
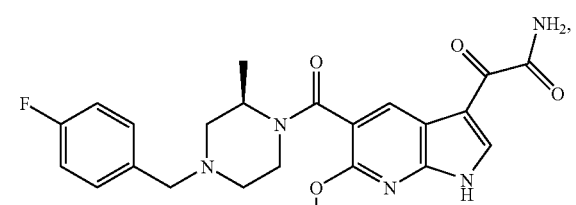
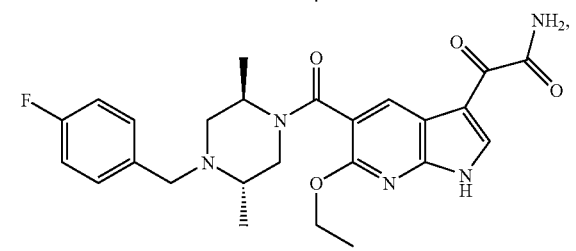
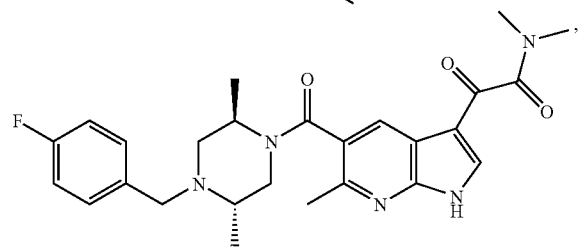
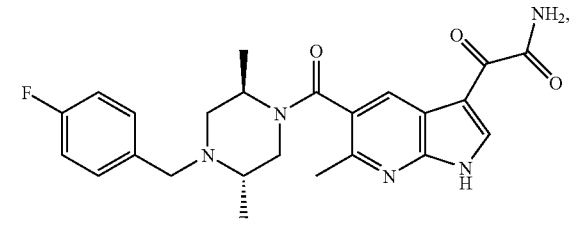
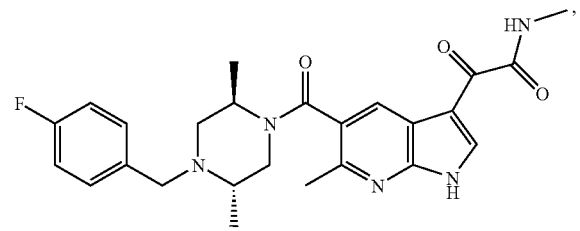
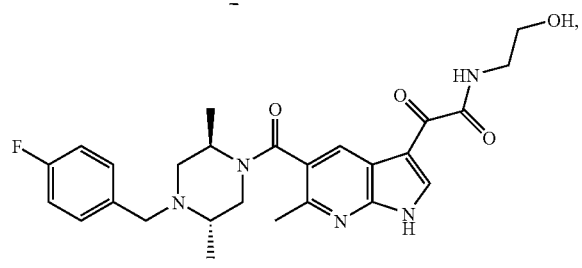
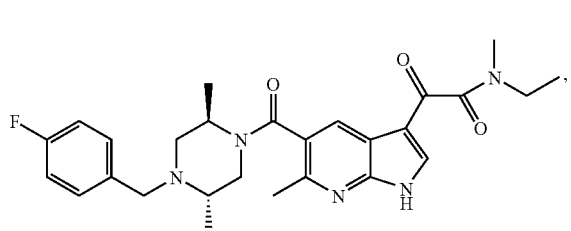
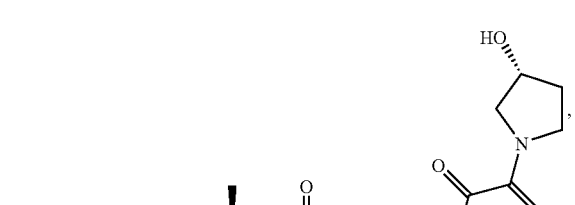
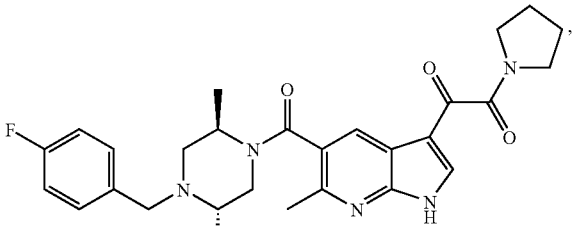
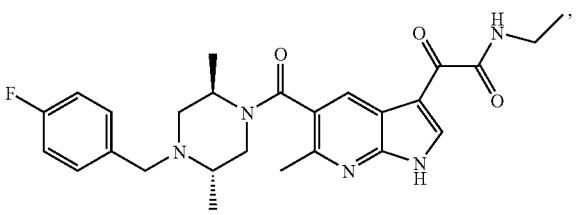
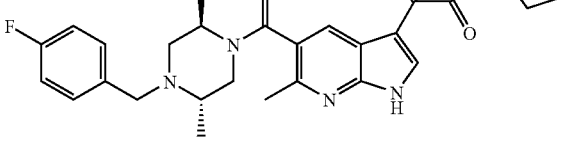

-continued
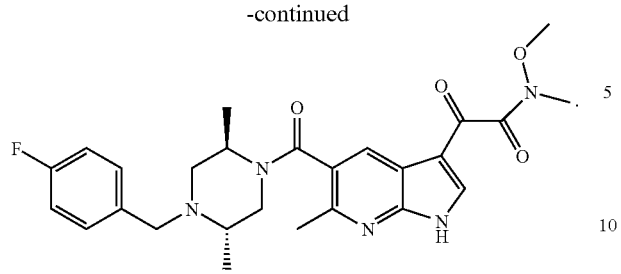
16. A pharmaceutical composition which composition comprises
a therapeutically effective amount of at least one compound of claim 1 and at least one pharmaceutically acceptable excipient.
* * * * *